(12) United States Patent
Py

(10) Patent No.: US 9,737,435 B2
(45) Date of Patent: Aug. 22, 2017

(54) DEVICE WITH CLOSURE, ONE-WAY VALVE, AND STORAGE CHAMBER AND RELATED METHOD

(71) Applicant: Daniel Py, Larchmont, NY (US)

(72) Inventor: Daniel Py, Larchmont, NY (US)

(73) Assignee: DR. PY INSTITUTE LLC, New Milford, CT (US)

(*) Notice: Subject to any disclaimer, the term of this patent is extended or adjusted under 35 U.S.C. 154(b) by 261 days.

(21) Appl. No.: 13/745,721

(22) Filed: Jan. 18, 2013

(65) Prior Publication Data
US 2013/0190704 A1 Jul. 25, 2013

Related U.S. Application Data

(60) Provisional application No. 61/589,259, filed on Jan. 20, 2012, provisional application No. 61/589,266, filed on Jan. 20, 2012.

(51) Int. Cl.
*A61F 9/00* (2006.01)
*B23P 15/00* (2006.01)
(Continued)

(52) U.S. Cl.
CPC .......... *A61F 9/0008* (2013.01); *B23P 15/001* (2013.01); *B05B 11/007* (2013.01);
(Continued)

(58) Field of Classification Search
CPC . B65D 83/0055; B65D 83/0022; F04B 45/02; A47K 5/1208; B05B 11/0067;
(Continued)

(56) References Cited

U.S. PATENT DOCUMENTS 4,039,103 A 8/1977 Juillet
5,025,957 A 6/1991 Ranalletta et al.
(Continued)

FOREIGN PATENT DOCUMENTS

RU 2277501 5/2003
RU 2225817 3/2004
(Continued)

OTHER PUBLICATIONS

International Search Report and Written Opinion of the International Searching Authority for International Application No. PCT/US13/22320, mailed Mar. 29, 2013.

*Primary Examiner* — Paul R Durand
*Assistant Examiner* — Andrew P Bainbridge
(74) *Attorney, Agent, or Firm* — McCarter & English, LLP

(57) ABSTRACT

A device has a first part with a valve seat and storage chamber, and a second part with a flexible valve cover and actuator. The storage chamber may be formed from a pre-form blow-molded into a flexible pouch defining a variable-volume storage chamber. The flexible valve cover and valve seat form a normally closed valve seam therebetween. The valve cover is movable in response to fluid at an inlet to the seam exceeding a valve opening pressure of the one-way valve between (i) a normally closed position with valve cover and valve seat in contact with each other and defining the normally closed seam, and (ii) a second position with at least a portion of the valve cover spaced away from the valve seat to allow the fluid to pass through the seam. The one-way valve may have anti-spritz features for using the device to dispense a substance, such as to the eye. The device may contain prostaglandins without the device material absorbing the prostaglandins material and/or without the material being adsorbed into the drug.

71 Claims, 14 Drawing Sheets

(51) Int. Cl.
*B05B 11/00* (2006.01)
*B65D 83/00* (2006.01)

(52) U.S. Cl.
CPC ....... *B05B 11/0056* (2013.01); *B05B 11/0062* (2013.01); *B05B 11/0067* (2013.01); *B05B 11/0097* (2013.01); *B65D 83/0022* (2013.01); *Y10T 29/49412* (2015.01)

(58) Field of Classification Search
CPC ............... B05B 11/0062; B05B 11/007; B05B 11/0056; B05B 11/0097; B23P 15/001; A61F 9/0008
USPC ..... 222/105, 207, 209; 29/890.124; 604/298
See application file for complete search history.

(56) References Cited

U.S. PATENT DOCUMENTS

| | | | |
|---|---|---|---|
| 5,190,190 A | | 3/1993 | Fudalla |
| 5,255,826 A | * | 10/1993 | Ranalletta ........... B05B 11/0021 222/209 |
| 5,641,004 A | * | 6/1997 | Py ........................... B65B 3/003 141/10 |
| 5,747,083 A | * | 5/1998 | Raymond et al. ............ 426/117 |
| 6,332,730 B1 | | 12/2001 | Taghavi-Khanghah |
| 6,334,551 B1 | | 1/2002 | Taghavi-Khanghah |
| 6,412,665 B1 | | 7/2002 | Taghavi-Khanghah |
| 6,745,763 B2 | * | 6/2004 | Webb ....................... 128/203.12 |
| 6,766,816 B2 | | 7/2004 | Secondo |
| 6,971,553 B2 | * | 12/2005 | Brennan ............. B05B 11/0059 222/207 |
| 7,032,631 B2 | * | 4/2006 | Py ................................. 141/82 |
| 7,513,396 B2 | | 4/2009 | Pardes et al. |
| 7,955,301 B1 | | 6/2011 | McKay |
| 8,132,695 B2 | * | 3/2012 | Py ........................... B65D 47/18 222/207 |
| 8,998,591 B2 | * | 4/2015 | Han de Man ........ A47K 5/1208 137/625.5 |
| 2004/0056054 A1 | | 3/2004 | Ottolangui |
| 2004/0140326 A1 | * | 7/2004 | Smart et al. .................. 222/192 |
| 2005/0006412 A1 | | 1/2005 | Albisetti et al. |
| 2006/0065677 A1 | * | 3/2006 | Py ........................... A45D 34/04 222/383.1 |
| 2008/0118299 A1 | * | 5/2008 | Py ........................... B65D 47/18 |
| 2009/0139883 A1 | * | 6/2009 | Py ............................. A61J 9/00 206/219 |
| 2009/0302064 A1 | | 12/2009 | Lavabre |
| 2010/0044395 A1 | * | 2/2010 | Webb ........................... 222/148 |
| 2010/0140290 A1 | * | 6/2010 | Py ........................... A45D 40/26 222/95 |
| 2010/0320226 A1 | * | 12/2010 | Nilsson ................ A47K 5/1209 222/207 |
| 2011/0084098 A1 | * | 4/2011 | Py ........................... B29B 11/08 222/207 |
| 2011/0284579 A1 | | 11/2011 | Pardes et al. |
| 2012/0014824 A1 | * | 1/2012 | Han de Man ........ A47K 5/1208 417/472 |

FOREIGN PATENT DOCUMENTS

| | | |
|---|---|---|
| RU | 2225818 | 3/2004 |
| WO | WO2008/061041 | 5/2008 |
| WO | WO2011/140508 | 11/2011 |

* cited by examiner

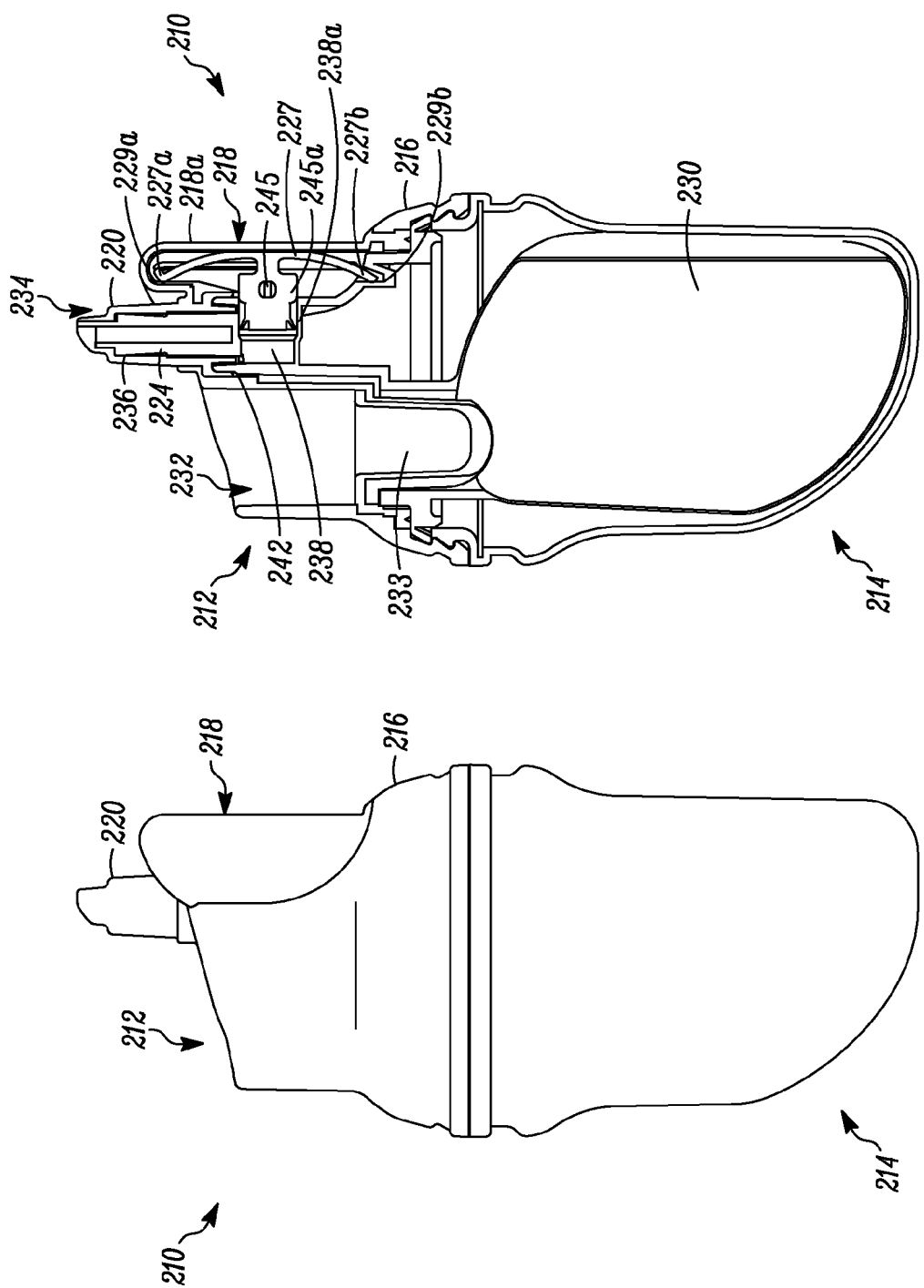

_US 9,737,435 B2_

DEVICE WITH CLOSURE, ONE-WAY VALVE, AND STORAGE CHAMBER AND RELATED METHOD

CROSS-REFERENCE TO RELATED APPLICATION

This patent application claims benefit under 35 U.S.C. §119 to U.S. Provisional Patent Application Nos. 61/589,259 and 61/589,266, filed Jan. 20, 2012, which are hereby incorporated by reference in their entireties as part of the present disclosure.

FIELD OF THE INVENTION

The present invention relates to devices with one-way valves and variable-volume storage chambers, and more particularly, to new and improved one-way valves, devices including one-way valves, anti-spritz features and/or variable-volume storage chambers, and to related methods.

BACKGROUND INFORMATION

Known devices including one-way valves and variable-volume storage chambers require the separate manufacture of the one-way valves, the closures, the variable-volume storage chambers, and the housings for receiving therein one or more such components. Such devices require the separate manufacture and assembly of multiple components, and in some instances, require sterilization of such multiple components prior to assembly. Such devices can be relatively expensive, and their manufacture relatively time-consuming and expensive.

Moreover, there a separate concern of aseptically filling a container after assembly of the multiple components. Known methods of filling can be difficult and inefficient. One of the drawbacks of such dispensers, and processes and equipment for filling such dispensers, is that the filling process is time consuming, and the processes and equipment are expensive. Further, the relatively complex nature of the filling processes and equipment can lead to more defectively filled dispensers than otherwise desired.

Another possible concern is that certain drugs and/or substances may be degraded or otherwise adversely affected by contacting a surface of the container in which it is stored. Depending on the materials used in constructing the container, the shelf-life of the drug or substance may be reduced and can lead to wasted substance. In the context of drugs and other rare or expensive substances (e.g., substances that are costly to produce), the monetary loss may be considerable.

Accordingly, it is an object of the present invention to overcome one or more of the above-described drawbacks and/or disadvantages.

SUMMARY OF THE INVENTION

In accordance with a first aspect, a device comprises a first piece including a storage chamber adapted for storing a substance therein, an outlet in fluid communication with the storage chamber, and an elongated generally annular valve seat and a second piece defining a closure configured to seal an interior of the storage chamber with respect to ambient atmosphere with the second piece engaged with the first piece, and including an elongated generally annular flexible valve member configured to sealingly engage the valve seat with the second piece engaged with the first piece to define a one way valve defining an elongated, generally annular, normally closed valve seam between the valve seat and the valve member, an inlet at one end of the seam, an outlet spaced relative to the inlet at another end of the seam, and a valve opening pressure. The valve member is moveable in response to substance at the inlet exceeding the valve opening pressure between (i) a first position with the valve member and valve seat forming the normally closed seam and (ii) a second position with at least a portion of the valve member spaced away from the valve seat to allow the substance to pass through the seam from the inlet through the outlet and out of the device.

In accordance with another aspect a device comprises first means for including second means for storing a substance therein, third means for sealing an interior of the second means with respect to ambient atmosphere with the third means engaged with the first means, and for including fourth means for sealingly engaging fifth means of the first means with the third means engaged with the first means to define sixth means having normally closed seventh means. The fourth means is also for moving in response to substance at an inlet to the seventh means exceeding a valve opening pressure of the sixth means from a first position forming the normally closed seventh means to a second position for allowing substance to pass through the sixth means and out of the device.

In accordance with another aspect, a one way valve has a relatively rigid valve seat. A flexible valve member is superimposed on the valve seat. The flexible valve cover and valve seat form a normally closed extending valve seam therebetween. In some embodiments, the seam extends axially and/or angularly (circumferentially). The valve seam defines an inlet at approximately one end thereof, and an outlet spaced, e.g., axially, relative to the inlet at approximately another end thereof. The valve cover and valve seat define a first degree of interference therebetween at the inlet, and a second degree of interference therebetween at the outlet that is less than the first degree of interference. The valve cover is movable in response to fluid at the inlet exceeding a valve opening pressure between (i) a normally closed position with the first and second mid-portions in contact with each other and defining the normally closed seam, and (ii) a second position with at least a portion of the valve cover spaced away from the valve seat to allow the fluid to pass through the seam from the inlet through the outlet.

In some embodiments, the degree of interference between the valve cover and valve seat progressively decreases from the first degree of interference to the second degree of interference. In some such embodiments, the degree of interference substantially uniformly decreases from the first degree of interference to the second degree of interference.

In some embodiments, in the normally closed position, the valve cover and valve seat form a hermetic seal therebetween. In some such embodiments, in the normally closed position, the hermetic seal substantially prevents the ingress of bacteria or germs in the direction from the outlet to the inlet. In some embodiments, the valve seat is curvilinear.

In accordance with another aspect, a flexible valve cover is formed of material with elastic properties and substantially zero creep. In some such embodiments, the material is a silicone. In some embodiments, the elastic material includes an antimicrobial additive. In some such embodiments, the elastic material is a relatively low durometer silicone including a silver-based antimicrobial additive.

In accordance with another aspect, a method comprises the following steps:

(i) providing a first piece including a storage chamber adapted for storing a substance therein, an outlet in fluid communication with the storage chamber, and an elongated generally annular valve seat;

(ii) providing a second piece defining a closure and an elongated generally annular flexible valve member;

(iii) engaging the first and second pieces together;

(iv) sealing an interior of the storage chamber with respect to ambient atmosphere with closure;

(v) superimposing the valve member onto the valve seat; and (vi) forming an elongated, generally annular, normally closed valve seam between the valve seat and the valve member.

In accordance with another aspect, a method comprises the following steps:

(i) injection molding a support and integral variable-volume storage chamber pre-form; and (ii) blow molding the pre-form, but not the support, into an expanded shape forming a pouch, at least a portion of which is flexible defining the variable-volume storage chamber.

In some embodiments, the method further comprises the following steps:

(i) collapsing the flexible pouch and the variable-volume storage chamber formed within the pouch;

(ii) sealing the interior of the variable-volume storage chamber with respect to ambient atmosphere; and (iii) sterilizing the sealed variable-volume storage chamber.

In further embodiments, the method further comprises the steps of molding a closure, and assembling the molded closure to the support to seal the variable-volume storage chamber with the closure. In some such embodiments, the step of molding the closure includes co-molding a support and integral flexible valve cover. In various embodiments, the flexible valve cover is formed from liquid silicone, which may be over-molded. In certain embodiments, the step of injection molding a support includes injection molding the support and integral valve seat. In some embodiments, the support is rigid. In further embodiments, the step of assembling the closure to the support includes superimposing the valve cover on the valve seat and forming the valve seam there between. In yet further embodiments, the closure is snapped onto the support. In some such embodiments, the closure defines, in a single piece, a peripheral rigid snapping ring and a central elastic member. The central elastic member may be a silicone member that has at least two portions: (i) a valve portion that extends as a bridge across the space left open in the center by the surrounding rigid snapping ring, and (ii) a depressible portion forming an actuator that may be manually or otherwise engageable for actuating the device and dispensing multiple doses through the valve. The configuration of the central elastic member is such that after assembly of the closure or second support onto the first support, the valve portion forms an interference fit with the nozzle segment of the pre-form, and the actuator is located above and/or spaced from a relatively rigid compression chamber segment of the pre-form. The bottom of the compression chamber is open in continuity with the inner channel of a hollow finger-like portion of the pre-form for blow molding into the flexible pouch.

In some embodiments, the step of molding the closure further includes co-molding a flexible actuator integral with the flexible valve cover, and the step of assembling the closure to the support further includes forming the compression chamber between the actuator and support that is connectable in fluid communication between the variable-volume storage chamber and the valve seam.

In some embodiments, the step of molding the closure includes co-molding an integral support and penetrable portion, and the assembling step includes assembling the closure to the support with the penetrable portion in fluid communication with the variable-volume storage chamber. Some such embodiments further comprise the steps of introducing an injection or filling member, such as a needle, through the penetrable portion after a pre-filling sterilizing step, introducing a substance through the injection member and into the variable-volume storage chamber, withdrawing the injection member from the penetrable portion, and resealing a resulting penetration aperture formed in the penetrable portion. In some such embodiments, the resealing step includes applying a liquid sealant to the resulting penetration aperture and hermetically resealing the penetrable portion with the liquid sealant. In some such embodiments, the liquid sealant is applied at approximately ambient temperature. In some such embodiments, the liquid sealant is a silicone and/or includes an anti-microbial additive and/or is loaded with metallic or other detectable particles.

In some embodiments, the sterilizing step includes irradiating the sealed, empty variable-volume storage chamber to sterilize the chamber. Some embodiments further comprise assembling the sealed closure and collapsed pouch assembly into a relatively rigid hollow body receiving the empty collapsed pouch therein. The sealed closure and collapsed pouch assembly may be sterilized prior to assembling same into the hollow body. In some embodiments, the collapsing step includes evacuating the pouch. The method further comprises sterile filling the collapsed pouch received within the hollow body. The method may include substantially preventing the formation of foam within the pouch during sterile filling thereof, such as by filling an evacuated or substantially evacuated variable-volume storage chamber.

Some embodiments further comprise the steps of applying to a surface of the closure and pouch assembly a fluid sterilant, and applying filtered gas at a temperature higher than ambient temperature to the fluid sterilant-receiving surface to further evaporate any fluid sterilant thereon. In some such embodiments, the fluid sterilant is applied to a penetrable portion of the closure, and the method further comprises the steps of introducing an injection or filling member through the penetrable portion after application of fluid sterilant and/or filtered gas thereto, introducing a substance through the injection member and into the variable-volume storage chamber, withdrawing the injection member from the penetrable portion, and resealing a resulting penetration aperture formed in the penetrable portion. In some such embodiments, the resealing step includes metering a liquid sealant onto the resulting penetration aperture and hermetically resealing the penetrable portion with the liquid sealant. Some such embodiments further comprise the step of forming the penetrable portion within a recess, and metering the liquid sealant into the recess to reseal the penetration aperture.

In accordance with another aspect, the present invention is directed to a device including a one-way valve, a first support forming the valve seat of the one-way valve thereon, and a variable-volume storage chamber extending outwardly from the first support such that substance in the chamber may be placed into fluid communication with the inlet to the valve seam. In some embodiments, the first support at least partially defines a compression chamber connectable in fluid communication between the variable-volume storage chamber and the inlet to the valve seam.

In accordance with another aspect, the first support is defined by an injection molded pre-form, and the variable-volume storage chamber is defined by a pouch at least a portion of which is flexible that is blow molded from the injection molded pre-form. Some embodiments further include a relatively rigid outer hollow recipient. The flexible pouch, which may be stretched blow molded from the pre-form, may be received within the hollow outer body, and the first support is fixedly secured to the body. Some embodiments further comprise a closure including a second support formed integral with the valve cover and fixedly connectable to the first support with the valve cover superimposed on the valve seat. In some embodiments, the first support at least partially defines a compression chamber connectable in fluid communication between the variable-volume storage chamber and the inlet to the valve seam, and the second support includes an actuator movable between rest, ambient or first and depressed, actuated or second positions for pressurizing or pumping fluid within the compression chamber above the valve opening pressure to, in turn, dispense the fluid through the one-way valve.

In some embodiments, the actuator is a flexible member formed integral with the valve cover. In some such embodiments, the valve cover and flexible actuator are co-molded with the second support. In some embodiments, the actuator defines a manually-engageable surface that is manually engageable and movable between the first and second positions. In some embodiments of the present invention, the closure defines a peripheral sealing member formed integral with the flexible valve member and actuator and forming a dry compression seal between the closure and first support. The first and second supports are sealingly engaged. In some embodiments, the first and second supports are snapped together to form a sealed enclosure. Such sub-assembly of the first and second supports forms itself essentially the whole liquid container, which can be sterilized after assembly. One of the advantages of this sub-assembly is that it is formed of only two parts forming a fluid-tight seal therebetween, and is further characterized by a collapsible pouch, which is collapsed, such as by vacuum, in order to reduce to a minimum the volume to be sterilized. It is particularly advantageous when such sterilization is achieved by radiation. Another advantage of such an enclosure sub-assembly is that it may include a clear transparent base, e.g., injection molded in one piece with the pre-form, which allows the use of high energy light for sterilization of the whole enclosure, such as a pulsed UV sterilizing radiation.

Some embodiments further comprise a penetrable portion configured to receive therethrough an injection or filling member for sterile filling the variable-volume storage chamber with a substance. The substance can take the form of any of numerous different substances that are currently known or that later become known, such as sterile foods or beverages, including without limitation milks, milk-based products and liquid nutrition products, drugs, pharmaceuticals, ophthalmic products, dermatological products, including creams, gels or other liquids of any desired viscosity, and nutritional supplements. Some embodiments further comprise a sealant or sealing layer overlying a resulting penetration aperture formed in the penetrable portion after removal of the injection member therefrom that hermetically seals the penetration aperture. In some such embodiments, the sealant is a liquid silicone. In some such embodiments, the liquid silicone is room-temperature curing. The liquid silicone or other sealant may be identical or substantially the same as a liquid silicone or other elastic material, that in some embodiments exhibits substantially zero creep, that is over molded on a relatively rigid snapping ring of the first support. One or more drops of the liquid silicone or other sealant used to seal the pin hole or other penetration aperture resulting from a piercing member for sterile filling may be blended with one or several of the following elements: (i) an antimicrobial additive, (ii) a colorant for visual inspection and quality control, and/or (iii) a metal or other detectable particles or substances loaded into the liquid silicone for in-line magnetic or other automated sensor detection of the amount of such particles or other detectable substance, and thus the amount of liquid silicone applied to reseal the penetration aperture. The liquid silicone or other sealant may be applied and received within a recess molded in an actuator or other surface of the device that defines the penetration region for sterile filling therethrough.

One advantage of the device and method of the present invention, and/or of the currently preferred embodiments thereof, is that the closure, valve cover and actuator may optionally be co-molded as a single part, the base defining the valve seat, compression chamber and variable-volume storage chamber pre-form can be injection molded as a single part, and therefore the device can be formed in essentially two parts that can be easily assembled, such as by snap fitting the closure to the base. Accordingly, the device can be manufactured with significantly fewer parts than known devices, yet can exhibit comparable or even greater functionality than such devices.

Another advantage is the capacity to fill viscous products and to re-seal at room temperature, even over a residue, due to the cavity being made for the purpose of sealing, and being made of the same material or substantially the same material as the sealant.

In certain embodiments, the elastic material of the penetrable portion is at least partially self-resealing. This property of the elastic and the relatively thick silicone actuator helps prevent any ingress immediately after filling until a more complete and permanent seal, e.g., a hermetic seal, may be provided by the liquid sealant or other sealing procedure. As a result, the sterile filling machine used to fill the device is relatively inexpensive, whether it includes a liquid sealant, a laser, or other thermal energy or radiation source for resealing, and/or involves the assembly of an additional part for mechanically resealing the resulting penetration aperture, such as providing a cover over the penetration.

Another substantial advantage is that the valve is extremely simple. The tension of the elastic valve segment after assembly onto the second support may be selected along with other valve characteristics to adjust for the viscosity of the product to be sealed within the device and dispensed through the valve. In relevant embodiments, any residue left in between the valve and the underlying nozzle is forced out by the interference/hoop stress differential between the valve and nozzle from the base to the dispensing tip of the valve.

Another advantage is that the elastic valve member is simple to assemble onto the rigid underlying nozzle of the enclosure and thereby provides a high quality product at a relatively inexpensive cost.

Another advantage is that a single, predetermined material may be selected for portions or surfaces of the device that will be in contact with the drug or substance throughout the shelf-life. The material can be selected to be compatible with the drug or substance and not adversely affect the substance. The material may be selected so that it is not adsorbed into the drug or substance or otherwise adversely affect it. Conversely, the material may be selected so that the drug or substance is not absorbed into the material. This increases the shelf-life of the drug or substances, and reduces the number of units which are defective or degraded.

Another substantial advantage is the relatively thin wall of the stretched blow-molded pouch, e.g., at its flexible portions. As a consequence, only a small amount of plastic is needed to form the liquid container itself, which further can be formed of only two pieces. Yet another advantage is that the outer housing or recipient can be made out of a fully bio-degradable material, of a re-usable material and/or an entirely recyclable material, knowing that the enclosure can be disassembled (including automatedly) from the outer recipient.

Other objects and advantages of the present invention, and/or of the currently preferred embodiments thereof, will become more readily apparent in view of the following detailed description of and accompanying drawings.

BRIEF DESCRIPTION OF THE DRAWINGS

FIG. 9 is a side elevational view of another embodiment of a device;

FIG. 10 is a cross-sectional view of the device of FIG. 9;

DETAILED DESCRIPTION OF EMBODIMENTS THE INVENTION

Figure 1:
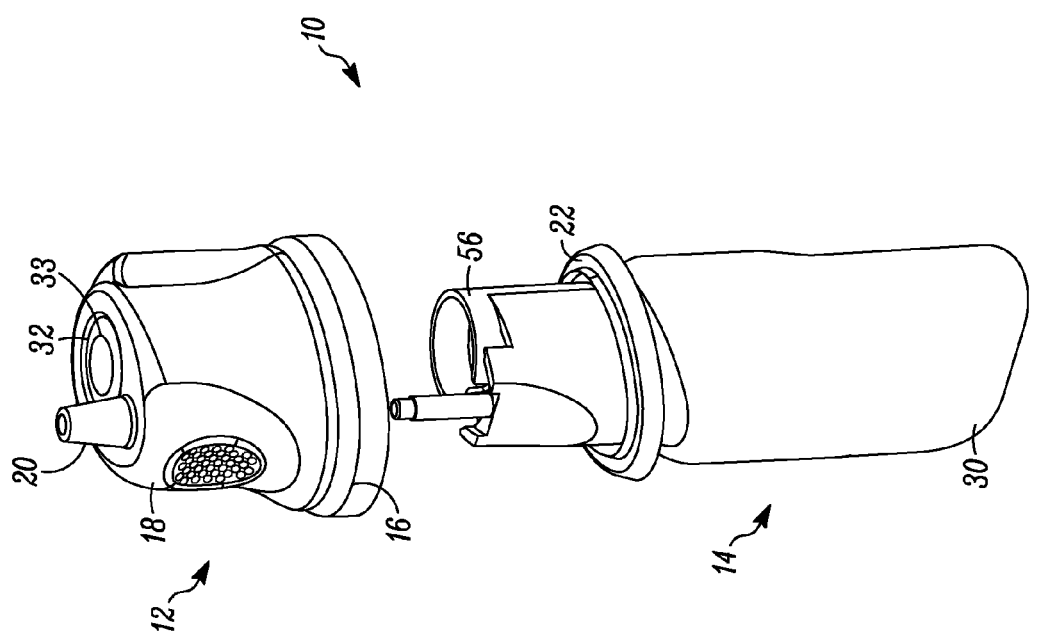
FIG. 1 is a perspective view of an unassembled device including a first piece and a second piece, the first piece including a first support and an actuator and the second piece including a variable-volume storage chamber, a second support and a boss.

In FIGS. 1-8C, a device embodying the present invention is indicated generally by the reference numeral 10. The device 10 includes a first piece 14 that is secured to a second piece 12 to form a sealed, empty device. The second piece 12 defines an integral second support 16, an actuator 18, and a flexible one-way valve or valve cover 20. The components of the second piece 12 are co-molded, such as by injection molding the second support 16, and over molding the actuator 18 and valve cover 20 to the second support 16. The first piece 14 includes a first support 22, a valve seat or nozzle 24, and a variable-volume storage chamber 30 formed from a pre-form 26. As described further below in connection with FIG. 3, the pre-form 26, but not the first support 22 and valve seat 24, is blow molded into a flexible pouch defining a variable-volume storage chamber 30.

The second piece 12 further defines a recess 32, which as described further below in connection with FIGS. 7 and 8, and a penetrable portion 33 that is penetrable by a needle or other injection or filling member to sterile or aseptically fill the variable-volume storage chamber 30. The recess 32 is adapted to receive a substantially metered amount of a liquid sealant, such as a silicone sealant, to hermetically seal the resulting penetration aperture and thereby hermetically seal the sterile filled substance within the variable-volume storage chamber 30.

Figure 4B:
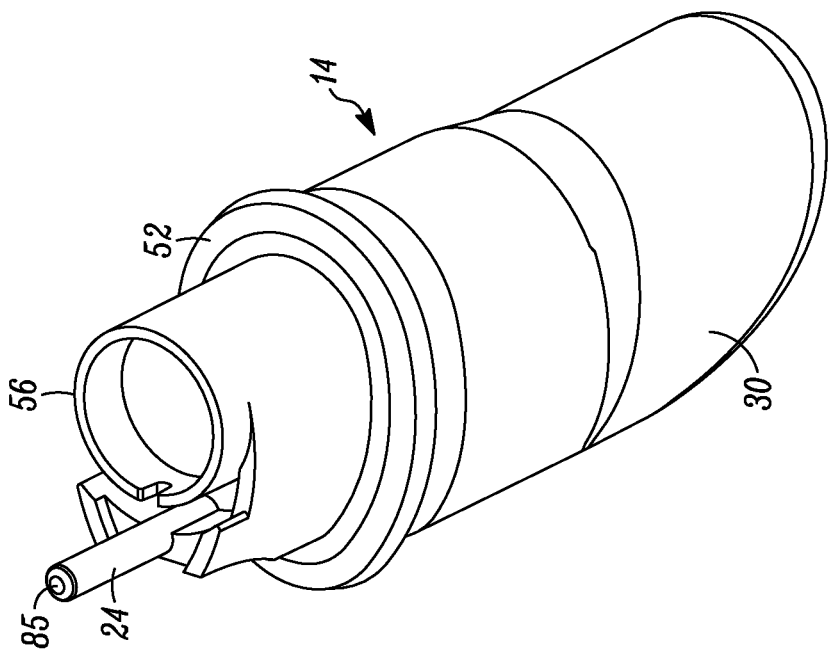
FIG. 4B is a perspective view of a second piece that engages with the first piece of FIG. 4A, the second piece including a second support, an annular flange, a boss and a valve seat having a recess.
Figure 4A:
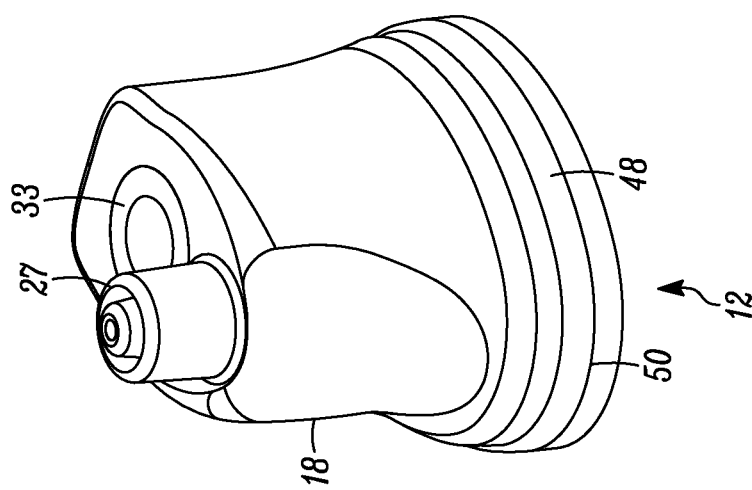
FIG. 4A is a perspective view of a first piece including an actuator, a flexible valve cover, a valve protector, an annular chamfer and annular grooves.

As described further below, the flexible valve cover 20 and relatively rigid valve seat 24 form a one-way valve 34 defining an elongated, normally closed interface or valve seam 36 therebetween. The second piece 12 and first piece 14 cooperate to define a compression chamber 38 that is connectable in fluid communication between the variable-volume storage chamber 30 and an inlet 40 to the normally closed valve seam 36 of the one-way valve 34. An annular check valve 42 is co-molded with the valve cover and actuator, and formed between the variable-volume storage chamber 30 and the compression chamber 38. As described further below, movement of the actuator 18 draws substantially metered amounts of the substance stored in the variable-volume storage chamber 30 through the check valve 42 and into the compression chamber 38 and, in turn, pressurizes the substance in the compression chamber 38 above a valve opening pressure to dispense the substance through the normally closed valve seam 36 of the one-way valve 34 and out of the device. The second piece 12 further defines a resilient sealing member 44 co-molded with the valve cover 20, actuator 18 and check valve 42, and extending about the periphery of the second piece 12. The first piece 14 defines a peripheral sealing surface 46 that engages the resilient sealing member 44 to form a compression seal therebetween to hermetically seal the interior of the device with respect to ambient atmosphere. The second support 16 defines on an interior surface thereof a first annular groove or recess 48 and an annular chamfer 50 formed adjacent to the first annular groove 48 (FIG. 4A). The first support 22 defines an annular flange 52 (FIG. 4B) that is received within the annular recess 48 of the second support 16 to fixedly secure the two supports together. The annular chamfer 50 facilitates movement of the first support 22 into the second support 16 and, in turn, snap fitting the annular flange 52 into the recess 48. Upon receiving the flange 52 into the recess 48, the sealing surface 46 compressively engages the sealing member 44 to form a dry, compression seal.

In the illustrated embodiment, the actuator 18 is formed of a resilient and/or elastomeric material. It will be understood the elastomeric materials described herein may include any suitable elastomer such as a thermoplastic elastomer and other elastomer alloys. The actuator 18 is shaped or configured so as to be pressed using a thumb or other digit. The actuator 18 defines a spring or resilient portion that allows the actuator to be depressed inwardly to compress the compression chamber 38 and, in turn, dispense substantially metered volumes of substance through the one-way valve 34. The first support 22 defines a boss 56 forming the inlet and outlet of the variable-volume storage chamber 30. The second piece 12 may likewise define an annular base 58 that is axially and radially spaced relative to the boss 56 to form an annular fluid-flow path therebetween. In some embodiments, the base 58 is cup-shaped and includes a non-collapsible area to reduce the ullage. The first support 22 defines an annular recess 60 that receives therein the annular base 58 of the spring 54. The annular recess 60 defines a fluid flow path between the variable-volume storage chamber 30 and the one-way check valve 42.

In order to actuate the device 10, the actuator 18 is depressed inwardly to compress the substance within the compression chamber 38 above the valve opening pressure. As the actuator 18 is depressed inwardly, the base 58 is moved axially inwardly, and radially outwardly within the annular recess 60 of the first support 22. This forces the resilient annular check valve 42 radially outwardly against the annular sealing surface of the first support 22 to thereby maintain the check valve 42 in the closed or sealed position, and in turn allow pressurization of the substance within the compression chamber 38 above the valve opening pressure. The annular recess 60 also operates to stop further axial and radial movement of the base 58 with further inward movement of the actuator 18 to thereby progressively decrease the volume of the compression chamber 38 as the actuator 18 is further depressed. When the substance within the compression chamber 38 exceeds the valve opening pressure, the substance is forced through the inlet 40 and normally closed seam 36 of the one-way valve 34 and out of the device. Then, the actuator 18 is released which, in turn, allows the spring of the actuator 18 and spring 54 to drive the actuator outwardly and into its ambient or rest first position. During movement from the depressed second position to the rest or ambient first position, the compression chamber 38 is expanded which, in turn, draws a substantially metered amount of substance from the variable-volume storage chamber 30, through the annular recess 60 and check valve 42, and into the compression chamber 38. The device 10 is then ready to dispense another metered amount of substance by repeating the foregoing steps. In some embodiments, the actuator 18 is manually engaged and depressed by a using the finger(s) of the same hand that is holding the device, or the device may be mounted within an apparatus known to those of ordinary skill in the pertinent art that includes an actuating device that engages the actuator 18 to depress the actuator.

Figure 2A:
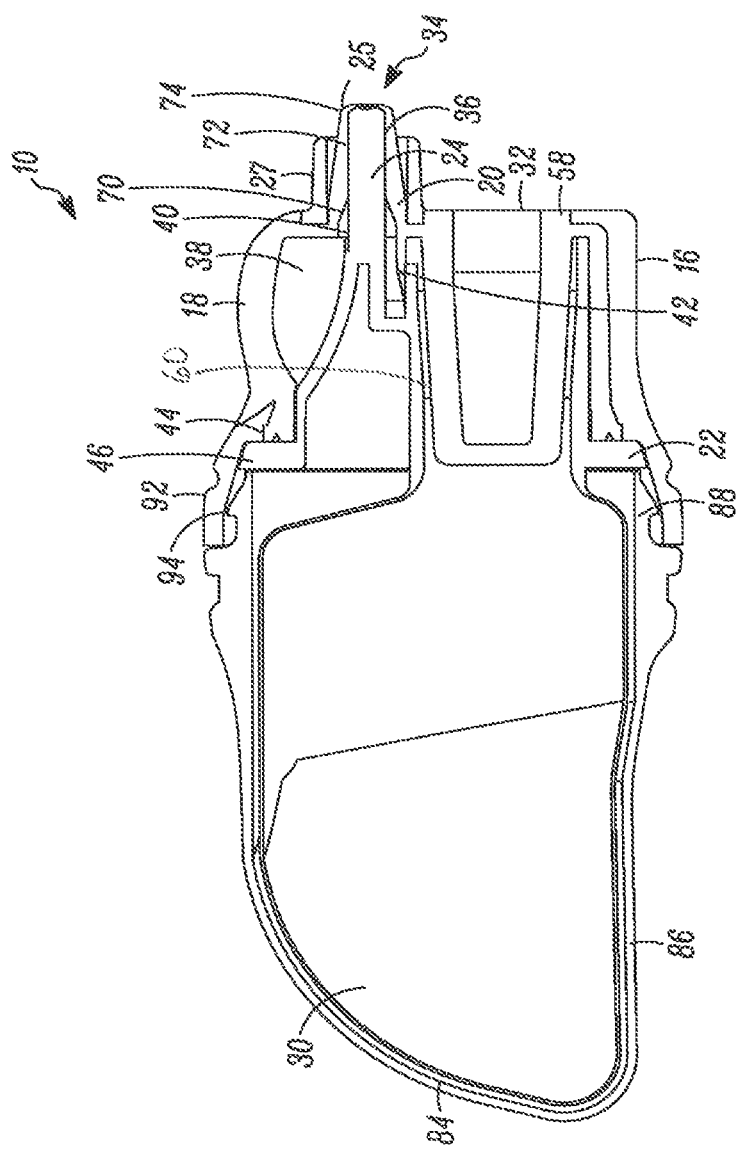
FIG. 2A is a cross-sectional view of the assembled device of FIG. 1 showing full engagement of the first piece with the second piece.

As shown best in FIG. 2A, the one way valve 34 comprises a generally cylindrical, relatively rigid valve seat 24. In some embodiments, the cylindrical valve seat 24 tapers outwardly as it approaches the annular flange 52. In some other embodiments, the cylindrical valve seat 24 is straight and does not taper. The valve seat 24 further includes a recess 85 at the tip of the valve seat 24. The tip instead may include a point to the valve seat 24 to prevent residue collection at the outlet. In some embodiments, the valve seat 24 includes a rough surface finish to avoid tackiness. Tackiness at the valve seat 24 can cause undesirable spritz of the substance dispensed from the one-way valve 34. Thus, in some embodiments the valve seat 24 includes a surface area selected to avoid tackiness, as will be understood by those of ordinary skill in the art.

In at least some embodiments, the flexible valve member 20 is configured to avoid spritz by including a deflector. The deflector 25 may include portions of the flexible valve member 20 that are wrapped or disposed over a top portion or end surface (at the downstream end) of the valve seat 24 to control the velocity of the substance exiting the one-way valve 34. In some embodiments, the deflector 25 is provided by having the flexible valve member 20 extending further than the valve seat 24 and being bent radially inward over a portion of the valve seat 24.

Thus, the flexible valve member 20 can be superimposed on the valve seat 24. As may be recognized by those of ordinary skill in the pertinent art based on the teachings herein, the valve seat and valve cover may define any of numerous other curvilinear shapes, any of numerous other combinations of curvilinear and flat shapes, and/or a substantially flat or planar shape. In the, illustrated embodiment, the flexible valve cover 20 and valve seat 24 form the normally closed axially and angularly extending valve seam 36 therebetween. The valve seam 36 defines an inlet 40 at approximately one end thereof, and an outlet 72 spaced, axially in the illustrated embodiment, relative to the inlet at approximately another end thereof. The valve cover 20 and valve seat 24 define a first degree of interference 70 therebetween at the inlet 40, and a second degree of interference 74 therebetween at the outlet 72 that is less than the first degree of interference 70. The valve cover 20 may be movable in response to fluid at the inlet 40 exceeding a valve opening pressure between (i) a normally closed position with first and second mid-portions in contact with each other and defining the normally closed seam 36, and (ii) a second or open position with at least a portion of the valve cover 20 spaced away from the valve seat 24 to allow the fluid or other substance to pass through the seam 36 from the inlet 40 through the outlet 72. For example, the pressurized fluid may cause axially spaced segments of the valve cover to sequentially move between the normally closed and open positions while the fluid moves from the inlet through the outlet of the valve.

In some embodiments, the degree of interference between the valve cover 20 and valve seat 24 may progressively decrease from the first degree of interference 70 to the second degree of interference 74. The degree of interference may also substantially uniformly decrease from the first degree of interference 70 to the second degree of interference 74. As can be seen, in the normally closed position, the valve cover 20 and valve seat 24 form a hermetic seal at the seam 36. In the illustrated embodiment, in the normally closed position, the hermetic seal substantially prevents the ingress of bacteria or germs in the direction from the outlet to the inlet.

In the illustrated embodiment, the flexible valve cover 20 is formed of an elastomeric material or thermoplastic elastomer that exhibits substantially zero creep. In one embodiment, the elastomeric material is a silicone. In another embodiment, the elastomeric material includes an antimicrobial additive to further prevent any bacteria, germs or other microbial substances from entering the seam 36 of the valve or otherwise collecting on the dispensing tip of the valve. In another embodiment, the elastomeric material is a silicone elastomer including a silver-based or other antimicrobial additive. Exemplary silicone elastomeric compounds for forming the valve cover and/or other features formed integral with the valve cover, including the actuator and sealing member, include any of numerous different liquid silicone rubbers, such as any of the liquid silicon rubbers sold by General Electric Company and/or Momentive Performance Materials under the LIM® trademark, including LIM 8040, or other liquid silicone rubbers, silicones or silicone-based elastomers, such as the antimicrobial elastomers sold by General Electric Company and/or Momentive Performance Materials under the StatSil™ trademark. In embodiments where the penetrable portion 33 is formed as one-piece with the actuator 18 and/or valve cover 20, the penetrable portion 33 is formed of the same material.

In other embodiments, the penetrable portion 33 is formed of a material, e.g., a silicone-based elastomer or thermoplastic elastomer, that is different from actuator 18 and/or valve cover 20. In some such embodiments, the penetrable portion 33 is co-molded with the actuator 18 and/or valve cover 20. In certain embodiments, the penetrable portion 33 is formed of a material that minimizes the formation of particles when penetrated by a filling member. This helps prevent contamination of the substance in the chamber 30. In some embodiments, the penetrable portion 30 includes a lubricant, e.g., a silicone oil or mineral oil, to reduce friction at the interface of the penetrable portion 30 and the filling member. In turn, this helps prevent particle formation.

In some embodiments as in the illustrated embodiment, the second piece 12 includes a valve shield or protector 27 for protecting the flexible valve cover 20 and the valve seat 24 from damage. In some embodiments, the valve protector 27 is in the form of an annular ring circumferentially disposed about the flexible valve cover 20. The valve protector 27 may be of the same length, shorter in length or longer than the valve seat 24. The valve protector 27 may be integrally formed with the second support 16 of the second piece 12. As best seen in FIG. 2A, the valve shield 27 is sufficiently spaced from the valve member 20 to permit the valve cover 20 to move away from the valve seat 24 and open the seam 36.

Figure 3:
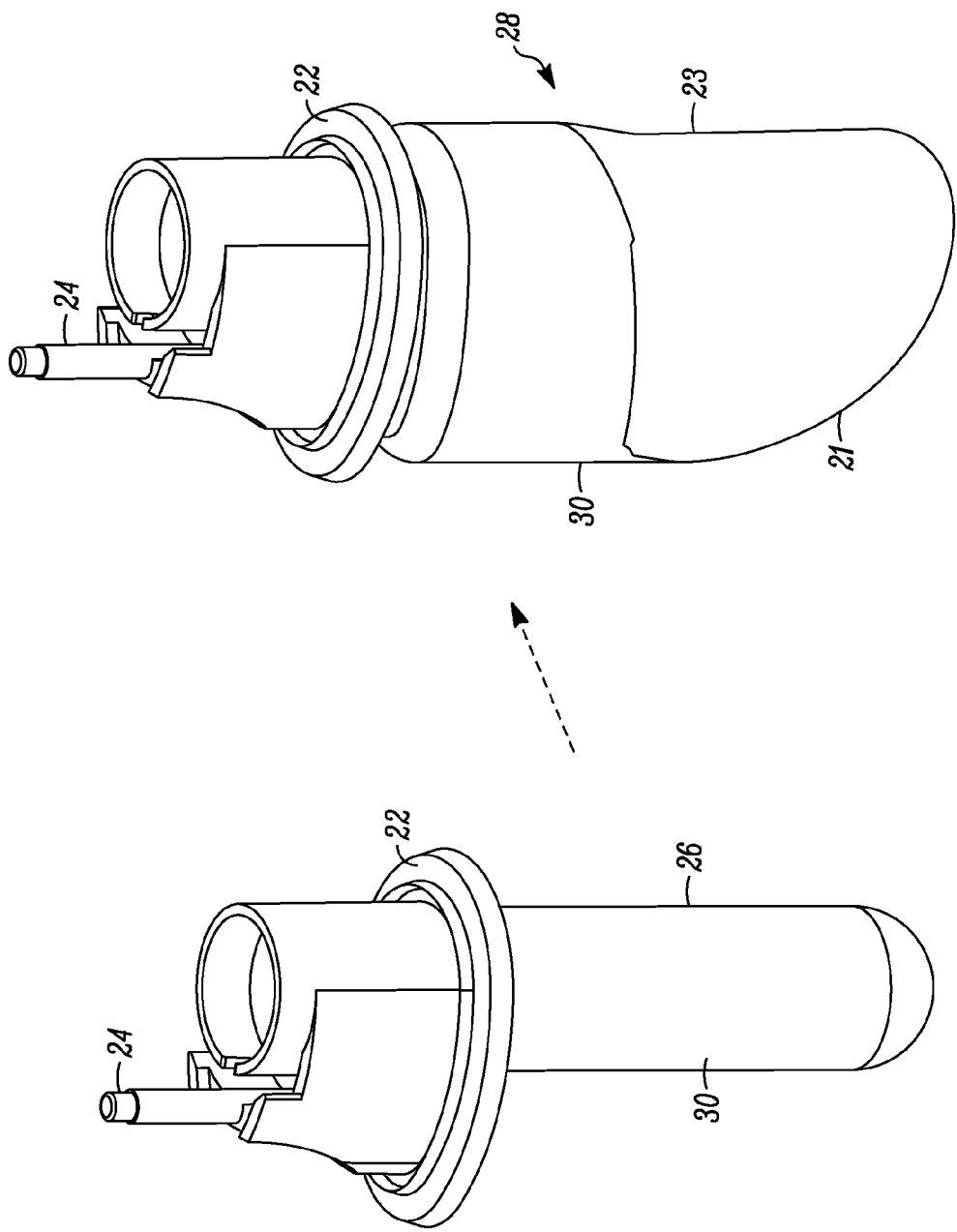
FIG. 3 is a perspective view of an injection molded variable-volume storage chamber pre-form, and showing pre-form blow molded into a flexible pouch forming the variable-volume storage chamber.

As shown typically in FIG. 3, the first piece 14 is formed from an injection molded pre-form 26, and the variable-volume storage chamber 30 is defined by a flexible pouch 28 blow molded from the injection molded pre-form 26. This may be accomplished in accordance with the teachings of any of the following co-pending patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Application No. 61/104,613, filed Oct. 10, 2008; and U.S. patent application Ser. No. 12/901,420, filed Oct. 8, 2010, entitled "Device with Co-Molded Closure, One Way Valve and Variable-Volume Storage Chamber, and Related Method," which claims the benefit of similarly titled U.S. Provisional Application No. 61/250,363, filed Oct. 9, 2009. A significant advantage of this feature is that the variable-volume storage chamber, valve seat, and part of the compression chamber, can be formed in one part as the first piece. Yet another advantage is that the valve seat and first support can be injection molded and formed to relatively tight tolerances, whereas the pre-form can be blow molded into the flexible pouch forming the variable-volume storage chamber while nevertheless maintaining the relatively tight tolerances of the other features of the first piece requiring such tolerances. As indicated in FIG. 3, after the first piece 14 is injection molded, the pre-form 26 is preheated and then stretch blow molded to form the pouch 28. In some embodiments, the pre-form 26 is stretch blow molded using micro-filtered air. This technique of using micro-filtered air may be useful in providing for a sterile flexible pouch 28. In the illustrated embodiment, the first piece 14 and thus the pre-form 26 is made of PET or PP (polypropylene). However, as may be recognized by those of ordinary skill in the pertinent art based on the teachings herein, these components may be made of any of numerous different materials, and may define any of numerous different layers of material(s), or combinations of different materials forming the different features of the first piece, that are currently known, or that later become known. For example, the first piece, or the pre-form thereof, may be defined by a multi-layered, or laminated material to provide the desired barrier properties and/or internal surfaces for contact with the product to be stored therein.

In some embodiments, the pre-form 26 is formed with a thickness that is thin enough to collapse onto itself. In at least some embodiments, only a portion of the pre-form 26 is configured to collapse onto itself. In some embodiments, the thickness of the walls of the flexible pouch 28 is 0.15 mm. In other embodiments, the thickness of the walls of the flexible pouch 28 is equal to or less than 0.25 mm. For example, after stretch blow molding the pre-form 26 is made into a pouch 28 that includes a first side 21 that is thin enough to collapse onto itself and a second side 23 that stays rigid. In some embodiments, the second side 23 stays rigid and has minimal stretch as compared to the first side 21. In at least some embodiments, the first side 21 is capable of collapsing toward the more rigid second side 23. After blow molding the pre-form into the pouch 28, the pouch is collapsed, such as by pulling a vacuum on the variable-volume storage chamber 30.

As shown in FIG. 2A, the second piece 12, which defines a device closure, is assembled to the first piece 14 to hermetically seal the variable-volume storage chamber 30 and form the one-way valve 34. As indicated above, the second piece or closure 12 is assembled to the first piece 14 by snap fitting the two parts at the peripheral flange 52 and first annular groove or recess 48. After assembly of the second and first pieces 12 and 14, respectively, the sealed empty device can be sterilized. In the illustrated embodiment, the device is sterilized by subjecting it to irradiation, such as ebeam or gamma radiation. However, as may be recognized by those of ordinary skill in the pertinent art based on the teachings herein, any of numerous different methods or apparatus for sterilizing the device and/or the internal surfaces and cavities thereof, that are currently known, or that later become known, equally may be employed.

By way of example, prior to filling the variable-volume storage chamber 30, the sealed empty chamber 30 may be sterilized by injecting a fluid sterilant therein, such as nitric oxide, with a needle or other injection member through the penetrable portion 33, and the needle employed for injecting the fluid sterilant and/or the substance to be sterile filled into the variable-volume storage chamber 30 may be a self opening and closing needle, in accordance with the teachings of any of the following co-pending patent applications, each of which is hereby expressly incorporated by reference in its entirety as part of the present disclosure: U.S. patent application Ser. No. 13/450,306, filed Apr. 18, 2012, entitled "Needle with Closure and Method," which claims the benefit of U.S. Provisional Patent Application No. 61/476,523, filed Apr. 18, 2011, entitled "Filling Needle and Method;" and U.S. patent application Ser. No. 13/529,951, filed Jun. 21, 2012, entitled "Fluid Sterilant Injection Sterilization Device and Method," which claims the benefit of U.S. Provisional Patent Application No. 61/499,626, filed Jun. 21, 2011, entitled "Nitric Oxide Injection Sterilization Device and Method."

In some embodiments, a single material is chosen to be in contact with the drug or substance throughout the shelf-life. If the active ingredient is absorbed into the plastic, then the device could fail. Alternatively, the material may be selected so that it is not adsorbed into the drug or substance. This increases the shelf-life of the drug or substances. This embodiment further reduces the number of units which are defective or degraded.

One possible use for these embodiments are for storing prostaglandins, a member of a group of lipid compounds that are derived enzymatically from fatty acids and used to treat glaucoma. One of the difficulties in storing or dispensing prostaglandins is that the active ingredient(s) is absorbed in thermoplastic elastomers and other elastomers and/or such plastics may leach into the prostaglandins. In some embodiments, the present embodiments overcome these problems by forming substantially all surfaces that are in contact with the drug out of polypropylene.

Additional members such as the internal polypropylene membrane or drug-protection portions 29 forming or disposed adjacent to the actuator 18, the check valve, the septum and other elastomeric portions are further used to reduce the elastomer-substance contact area. In some embodiments, the area is reduced to substantially zero.

Thus, the pre-form 26 and any other surfaces that contacts the drug or substance may be formed using polypropylene, reducing the contact with elastomers and the risk or absorption of the drug or adsorption of the material. In some embodiments, the only contact with the elastomer occurs during the passage of the drop through the valve, a brief time period that does not affect the efficacy of the drug or substance or the integrity of the device.

Figure 2B:
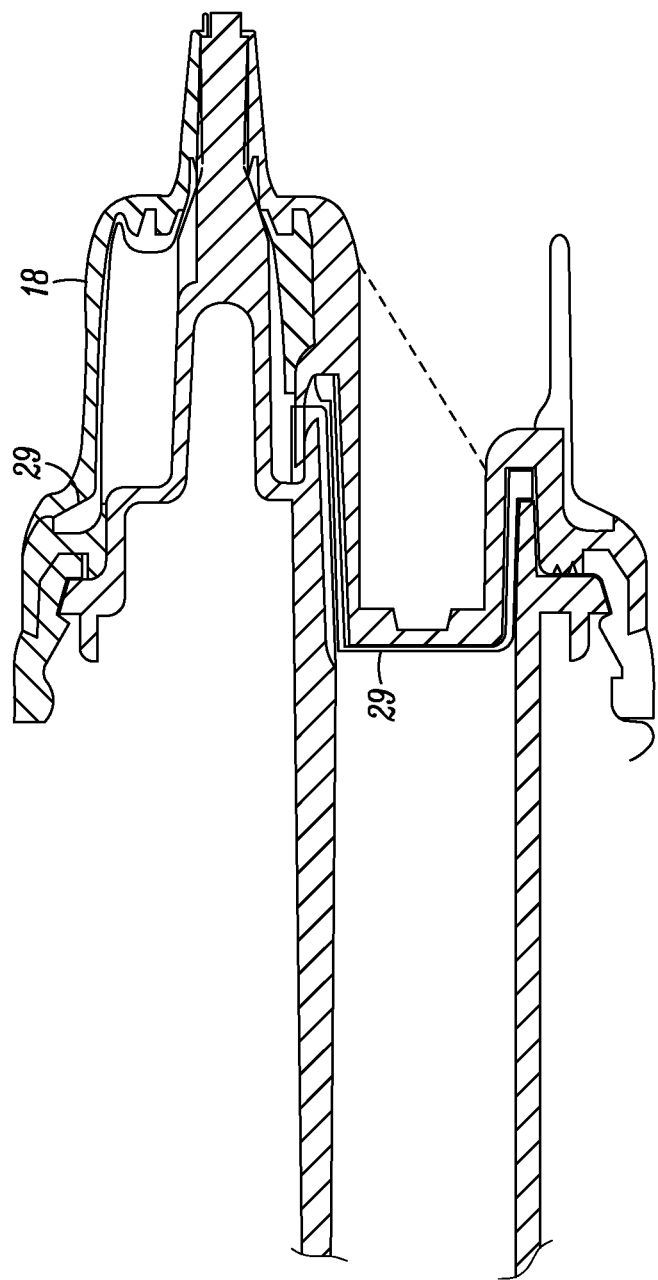
FIG. 2B is a cross-sectional view of an assembled device similar to that of FIG. 2A but having additional drug protection portions.

In at least some other embodiments, additional portions may be added to the second piece 12 and/or first piece 14 to reduce the contact of certain drugs with an elastomer or silicone. In some embodiments, the device 10 may be used in ophthalmic applications to deliver prostaglandins or some other therapy or drug for treating glaucoma. The therapy or medication, such as is the case with prostaglandins may be sensitive to or adversely react with elastomers. In some applications, the term drug is be used to describe any therapy, compound or drug contained within the device 10. In such applications, it is useful to utilize drug-protective portions 29. As seen in FIG. 2B, the drug-protection portions 29 are rigid portions introduced onto the second piece 12 or first piece 14 to reduce drug contact with an elastomer. In at least some embodiments, the drug-protection portions 29 are formed of polypropylene. As seen in FIG. 2B, the drug-protection portions 29 may be located beneath or underneath actuator 18. The drug-protection portions 29 may also be located between the recess 32 and the storage chamber 30. Portions of the drug-protection portions 29 may also be used adjacent the check valve 42 and in other locations where the drug contacts an elastomer. It will be noted that in such applications, the pre-form 26 may be modified to include portions for mating with or coupling to the rigid pieces of the drug-protection portions 29. Furthermore, it will be understood that such drug-protection portions 29 may be integrally formed with the second support 16 of the second piece 12.

The drug-protection portions 29 may be formed as thin as possible in order to allow the actuator 18 to function as required. Accordingly, the drug-protection portions may be flexible. In some embodiments, the drug-protection portions 29 are formed by compression molding. In at least some other embodiments, only drug-protection portions 29 under the actuator 18 and the recess 32 are compression molded. The elastomeric portions (e.g. the actuator 18, check valve 42 and one-way valve 34) may be overmolded onto the rigid components, including the drug-protection portions 29. In some embodiments, the rigid components and the elastomeric components are insert molded or sequential injection molded to form a single second piece 12 UV light may be applied to the rigid components and elastomeric components before and during assembly to sterilize the components and reduce germs. In some embodiments, sterilization is accomplished through pulsed UV light sterilization being applied from at least two directions. In some embodiments, the UV sterilization is applied from the top and bottom of the second piece 12. Alternatively, the second piece 12 may be assembled under an overpressure of sterile air or other gas following UV sterilization.

The device 10 may further include a relatively rigid, hollow body or housing 84. The flexible pouch 28 is received within the hollow body 84, and the second support 16 is fixedly secured to the body. The housing 84 includes a base 86 and an upper support 88 that is secured to the second support 16 of the closure to attach the housing to the closure. As shown in FIGS. 4A and 4B, the second support 16 defines a first annular groove 48 for receiving the annular flange 52 of the first piece 14 and securing the second piece 12 to the first piece 14. The upper support 88 of the housing may define an outwardly extending, substantially annular flange 94 that is received within a second annular groove 92 in the second piece 12 to secure the housing to the assembled second piece 12. In the illustrated embodiment, the annular flange 94 is press fit within the second annular groove 92; however, as may be recognized by those of ordinary skill in the pertinent art based on the teachings herein, the flange 94 or housing 84 can be secured to the closure or second and/or first supports in any of numerous different ways that are currently known, or that later become known. Thus, the second piece may include a plurality of snap levels, for example, two snap levels, each snap level having its own annular groove for coupling with the second piece and the housing, respectively. It will be understood that the phrase "annular groove" does not limit the shape of the groove of the second piece. Instead, the phrase "annular groove" may mean any recess formed in the second piece to receive a flange, rib or member, the recess being formed in any shape and extending fully or partially around the inner circumference of the second piece 12.

In some embodiments, the sealed, empty, sterilized device is then readied for sterile or aseptic filling by again sterilizing the penetrable portion 33 of the device (e.g., in case such surfaces are contaminated during transport or assembly post sterilization of the device). First, a fluid sterilant, such as vaporized hydrogen peroxide, is applied to the penetrable portion 33 to re-sterilize such surface(s). Second, a heated filtered gas, such as air, is applied to the fluid-sterilant receiving surface(s) to further evaporate such sterilant and provide a dry, sterilized, penetrable surface.

Figure 5B:
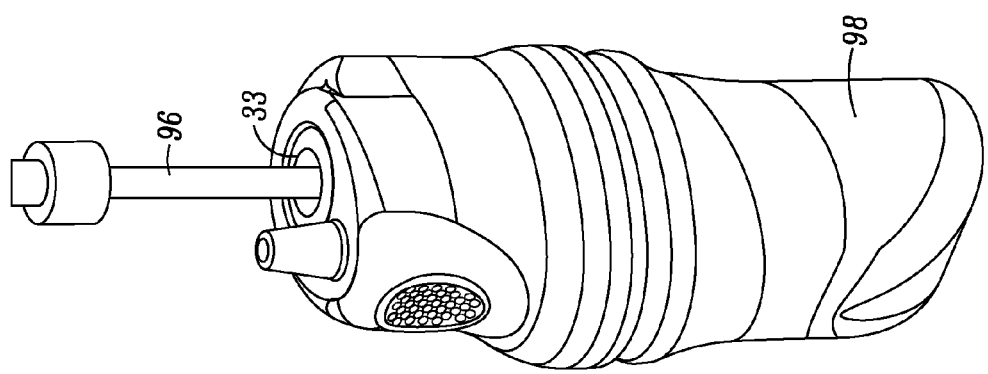
FIGS. 5A and 5B are sequential, perspective views of the assembled dispenser undergoing filling of the variable-volume storage chamber.
Figure 5A:
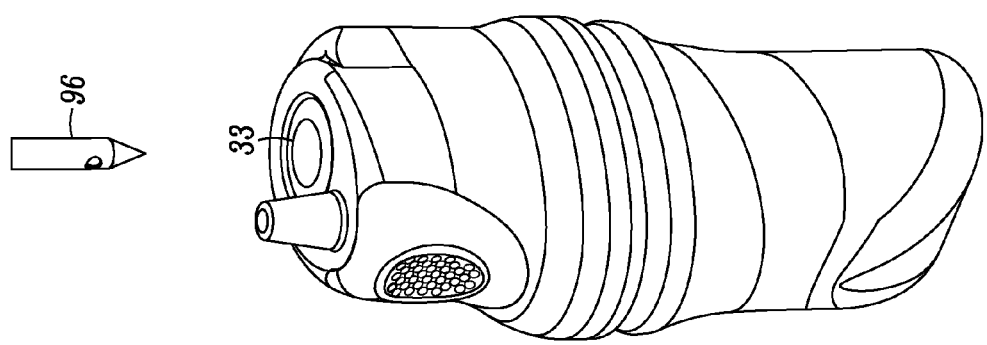

As shown in FIGS. 5A and 5B, the sealed, empty sterile device is then sterile or aseptically filled by introducing an injection member, such as a needle 96, through the penetrable portion 33 at the base of the recess 32, introducing a substance 98 through the injection member and into the variable-volume storage chamber 30, withdrawing the injection member 96 from the penetrable portion 33, and resealing a resulting penetration aperture formed in the penetrable portion 33. In some embodiments, INTACT™ filling is used to fill the sealed, empty sterile device.

One advantage of collapsing the pouch 28 prior to filling is that there is very little, or even substantially no air in the variable-volume storage chamber 30 prior to filling, thus preventing or substantially preventing the formation of foam during filling of a liquid substance 98 into the variable-volume chamber. This can be a significant advantage with respect to increasing filling speeds, particularly with liquid substances that have a tendency to foam during filling, such as with liquid foods and beverages, such as milks or milk-based products, and other liquid products. Accordingly, the device and method of the present invention can provide significantly increased filling speeds in comparison to the prior art.

Figure 6A:
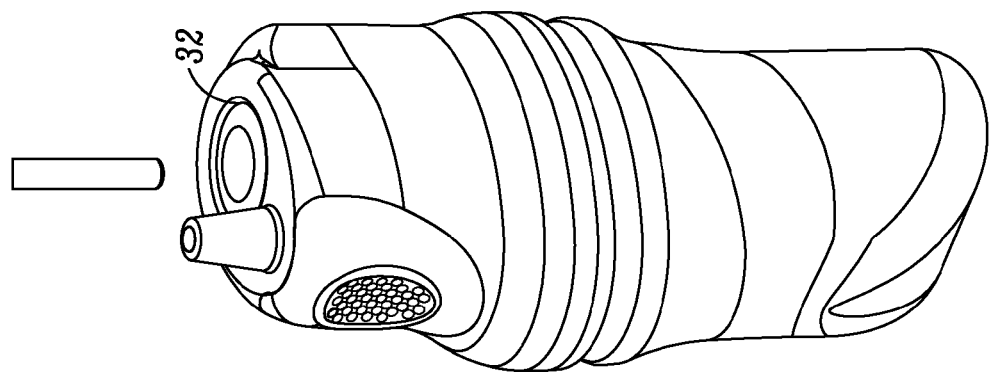
FIGS. 6A and 6B are sequential, perspective views illustrating resealing of the resultant penetration aperture with a liquid sealant, such as a room temperature vulcanizing silicone sealant, to hermetically reseal the closure and sterile product within the variable-volume storage chamber.
Figure 6B:
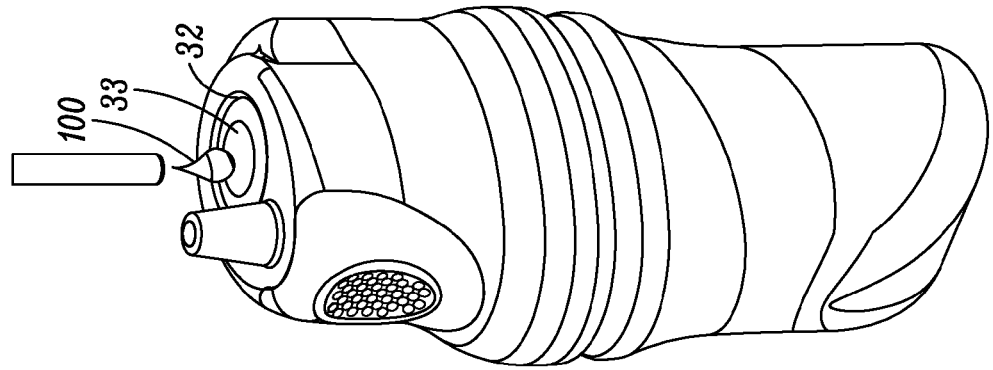

In the illustrated embodiment, and as shown in FIGS. 6A and 6B, the resealing step includes applying a liquid sealant 100 to the resulting penetration aperture formed in the recess 32 and hermetically resealing the penetrable portion 33 with the liquid sealant. The sealing may be performed in accordance with the teachings of any of the following patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Patent Application Ser. No. 61/104,613, filed Oct. 10, 2008; U.S. patent application Ser. No. 12/901,420, filed Oct. 8, 2010, entitled "Device with Co-Molded One-Way Valve and Variable Volume Storage Chamber and Related Method," which claims the benefit of similarly titled U.S. Provisional Patent Application No. 61/250,363, filed Oct. 9, 2009; and U.S. patent application Ser. No. 13/450,306, filed Apr. 18, 2012, entitled "Needle with Closure and Method," which claims the benefit of U.S. Provisional Patent Application No. 61/476,523, filed Apr. 18, 2011, entitled "Filling Needle and Method." In the illustrated embodiment, the liquid sealant is applied at approximately ambient temperature. In the currently illustrated embodiment, the liquid sealant is a silicone. However, as may be recognized by those of ordinary skill in the pertinent art based on the teachings herein, the liquid sealant can take the form of any of numerous different sealants that are currently known, or that later become known, e.g., glue, epoxy, etc.

Figure 7A:
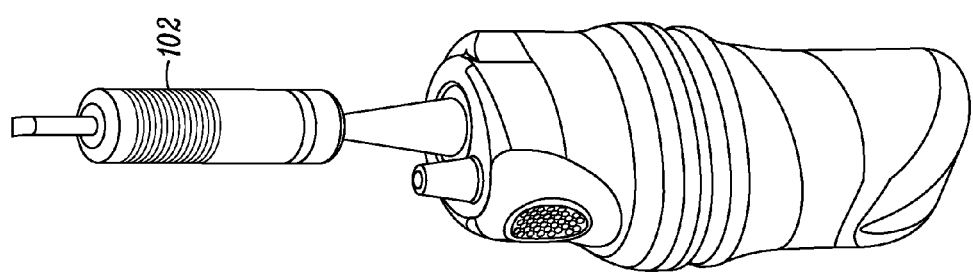
FIGS. 7A and 7B are sequential, perspective views illustrating curing of liquid sealant to hermetically reseal the closure and sterile product within the variable-volume storage chamber.
Figure 7B:
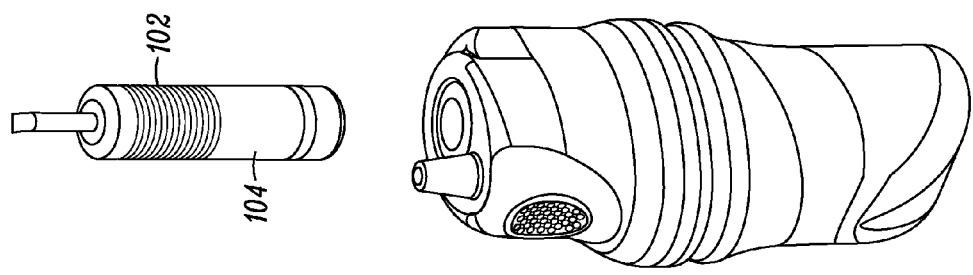

As can be seen in FIGS. 7A and 7B, a resealing device 102 is mounted over the devices to be resealed after filling. The resealing device 102 includes a source of liquid sealant 100, or is coupled in fluid communication with a source of liquid sealant, and a pump for pumping metered amounts of the liquid sealant onto the penetrated regions of the devices to hermetically reseal the penetration apertures, and thus hermetically seal the aseptically filled product within the variable-volume storage chamber 30. The pump 104 may take the form of a piston-type pump as is the illustrated embodiment, or may take the form of any of numerous other mechanisms for metering volumes or other measured amounts of liquid sealant onto the penetration apertures of the devices to seal the apertures, that are currently known, or that later become known, such as systems with pressurized liquid sealant and valves for releasing the pressurized sealant. The resealing device 102 may be fixedly mounted over a motorized conveyor for transporting the devices 10, or may be movable relative to the devices, to align a dispensing port of the device with the penetration aperture(s). An overpressure of sterile filtered air of other gas may be supplied into a chamber or barrier enclosure containing the needle(s) and liquid resealing device(s) to further prevent contamination of devices during the needle filling and liquid resealing process. If desired, the system may include a plurality of needles mounted on a manifold that is driven vertically, or on which the needles are driven vertically, into and out of engagement with the penetrable portions of the devices, and a plurality of liquid resealing devices mounted adjacent to, or downstream of, the needles for liquid resealing the penetration apertures.

Alternatively, the penetration aperture can be sealed by the application of radiation or energy, e.g., laser radiation or thermal energy, in accordance with the teachings of any of the following patents and patent applications, each of which is hereby expressly incorporated by reference in its entirety as part of the present disclosure: U.S. patent application Ser. No. 12/254,789, filed Oct. 20, 2008, entitled "Container Having a Closure and Removable Resealable Stopper for Sealing a Substance Therein and Related Method," which, in turn, claims the benefit of U.S. Patent Application No. 60/981,107, filed Oct. 18, 2007, entitled "Container Having a Closure and Removable Resealable Stopper for Sealing a Substance Therein;" U.S. patent application Ser. No. 12/245,678, filed Oct. 3, 2008, entitled "Apparatus For Formulating and Aseptically Filling Liquid Products," and U.S. patent application Ser. No. 12/245,681, filed Oct. 3, 2008, entitled "Method For Formulating and Aseptically Filling Liquid Products," which, in turn, claim the benefit of U.S. Patent Application Ser. No. 60/997,675, filed Oct. 4, 2007, entitled "Apparatus and Method for Formulating and Aseptically Filling Liquid Products;" U.S. patent application Ser. No. 12/875,440, filed Sep. 3, 2010, entitled "Device with Needle Penetrable and Laser Resealable Portion and Related Method," now U.S. Pat. No. 7,980,276, which is a divisional of U.S. patent application Ser. No. 12/371,386, filed Feb. 13, 2009, entitled "Device with Needle Penetrable and Laser Resealable Portion," now U.S. Pat. No. 7,810,529, which is a continuation of U.S. patent application Ser. No. 11/949,087, filed Dec. 3, 2007, entitled "Device with Needle Penetrable and Laser Resealable Portion and Related Method," now U.S. Pat. No. 7,490,639, which is a continuation of similarly titled U.S. patent application Ser. No. 11/879,485, filed Jul. 16, 2007, now U.S. Pat. No. 7,445,033, which is a continuation of similarly titled U.S. patent application Ser. No. 11/408,704, filed Apr. 21, 2006, now U.S. Pat. No. 7,243,689, which is a continuation of U.S. patent application Ser. No. 10/766,172, filed Jan. 28, 2004, entitled "Medicament Vial Having a Heat-Sealable Cap, and Apparatus and Method for Filling the Vial," now U.S. Pat. No. 7,032,631, which is a continuation-in-part of similarly titled U.S. patent application Ser. No. 10/694,364, filed Oct. 27, 2003, now U.S. Pat. No. 6,805,170 which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application Ser. No.

60/182,139, filed Feb. 11, 2000, and similarly titled U.S. Provisional Patent Application Ser. No. 60/443,526, filed Jan. 28, 2003, and similarly titled U.S. Provisional Patent Application Ser. No. 60/484,204, filed Jun. 30, 2003; U.S. patent application Ser. No. 13/193,662, filed Jul. 29, 2011, entitled "Sealed Contained and Method of Filling and Resealing Same," which is a continuation of U.S. patent application Ser. No. 12/791,629, filed Jun. 1, 2010, entitled "Sealed Containers and Methods of Making and Filling Same," now U.S. Pat. No. 7,992,597, which is a divisional of U.S. patent application Ser. No. 11/515,162, filed Sep. 1, 2006, entitled "Sealed Containers and Methods of Making and Filling Same," now U.S. Pat. No. 7,726,352, which is a continuation of U.S. patent application Ser. No. 10/655,455, filed Sep. 3, 2003, entitled "Sealed Containers and Methods of Making and Filling Same," now U.S. Pat. No. 7,100,646, which is a continuation-in-part of U.S. patent application Ser. No. 10/393,966, filed Mar. 21, 2003, entitled "Medicament Vial Having A Heat-Sealable Cap, and Apparatus and Method For Filling The Vial," now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application Ser. No. 60/182,139, filed on Feb. 11, 2000, and U.S. Provisional Patent Application Ser. No. 60/408,068, filed Sep. 3, 2002, entitled "Sealed Containers and Methods Of Making and Filling Same;" U.S. patent application Ser. No. 12/627,655, filed Nov. 30, 2009, entitled "Adjustable Needle Filling and Laser Sealing Apparatus and Method," now U.S. Pat. No. 8,096,333, which is a continuation of similarly titled U.S. patent application Ser. No. 10/983,178, filed Nov. 5, 2004, now U.S. Pat. No. 7,628,184, which, in turn, claims the benefit of U.S. Provisional Patent Application Ser. No. 60/518,267, filed Nov. 7, 2003, entitled "Needle Filling and Laser Sealing Station," and similarly titled U.S. Provisional Patent Application Ser. No. 60/518,685, filed Nov. 10, 2003; U.S. patent application Ser. No. 11/901,467, filed Sep. 17, 2007 entitled "Apparatus and Method for Needle Filling and Laser Resealing," which is a continuation of similarly titled U.S. patent application Ser. No. 11/510,961 filed Aug. 28, 2006, now U.S. Pat. No. 7,270,158, which is a continuation of similarly titled U.S. patent application Ser. No. 11/070,440, filed Mar. 2, 2005; now U.S. Pat. No. 7,096,896, which, in turn, claims the benefit of U.S. Provisional Patent Application Ser. No. 60/550,805, filed Mar. 5, 2004, entitled 'Apparatus for Needle Filling and Laser Resealing;" U.S. patent application Ser. No. 12/768,885, filed Apr. 28, 2010, entitled "Apparatus for Molding and Assembling Containers with Stoppers and Filling Same," now U.S. Pat. No. 7,975,453, which is a continuation of similarly titled U.S. patent application Ser. No. 11/074,513, filed Mar. 7, 2005, now U.S. Pat. No. 7,707,807, which claims the benefit of U.S. Provisional Patent Application Ser. No. 60/551,565, filed Mar. 8, 2004, entitled "Apparatus and Method For Molding and Assembling Containers With Stoppers and Filling Same;" U.S. patent application Ser. No. 12/715,821, filed Mar. 2, 2010, entitled "Method for Molding and Assembling Containers with Stopper and Filling Same," now U.S. Pat. No. 8,112,972, which is a continuation of similarly titled U.S. patent application Ser. No. 11/074,454, filed Mar. 7, 2005, now U.S. Pat. No. 7,669,390; U.S. patent application Ser. No. 11/339,966, filed Jan. 25, 2006, entitled "Container Closure With Overlying Needle Penetrable and Thermally Resealable Portion and Underlying Portion Compatible With Fat Containing Liquid Product, and Related Method," now U.S. Pat. No. 7,954,521, which, in turn, claims the benefit of U.S. Provisional Patent Application Ser. No. 60/647,049, filed Jan. 25, 2005, entitled "Container with Needle Penetrable and Thermally Resealable Stopper, Snap-Ring, and Cap for Securing Stopper;" U.S. patent application Ser. No. 12/861,354, filed Aug. 23, 2010, entitled "Ready To Drink Container With Nipple and Needle Penetrable and Laser Resealable Portion, and Related Method;" which is a divisional of similarly titled U.S. patent application Ser. No. 11/786,206, filed Apr. 10, 2007, now U.S. Pat. No. 7,780,023, which, into turn, claims the benefit of similarly titled U.S. Provisional Patent Application Ser. No. 60/790,684, filed Apr. 10, 2006; U.S. patent application Ser. No. 11/295,251, filed Dec. 5, 2005, entitled "One-Way Valve, Apparatus and Method of Using the Valve," now U.S. Pat. No. 7,322,491, which, in turn, claims the benefit of similarly titled U.S. Provisional Patent Application Ser. No. 60/644,130, filed Jan. 14, 2005, and similarly titled U.S. Provisional Patent Application Ser. No. 60/633,332, filed Dec. 4, 2004; U.S. patent application Ser. No. 12/789,565, filed May 28, 2010, entitled "Resealable Containers and Methods of Making, Filling and Resealing the Same," which is a continuation of U.S. patent application Ser. No. 11/933,272, filed Oct. 31, 2007, entitled "Resealable Containers and Assemblies for Filling and Resealing Same," now U.S. Pat. No. 7,726,357, which is a continuation of U.S. patent application Ser. No. 11/515,162, filed Sep. 1, 2006, entitled "Sealed Containers and Methods of Making and Filling Same," now U.S. Pat. No. 7,726,352; U.S. patent application Ser. No. 13/045,655, filed Mar. 11, 2011, entitled "Sterile Filling Machine Having Filling Station and E-Beam Chamber," which is a continuation of U.S. patent application Ser. No. 12/496,985, filed Jul. 2, 2009, entitled "Sterile Filling Machine Having Needle Filling Station and Conveyor," now U.S. Pat. No. 7,905,257, which is a continuation of U.S. patent application Ser. No. 11/527,775, filed Sep. 25, 2006, entitled "Sterile Filling Machine Having Needle Filling Station within E-Beam Chamber," now U.S. Pat. No. 7,556,066, which is a continuation of similarly titled U.S. patent application Ser. No. 11/103,803, filed Apr. 11, 2005, now U.S. Pat. No. 7,111,649, which is a continuation of similarly titled U.S. patent application Ser. No. 10/600,525, filed Jun. 19, 2003, now U.S. Pat. No. 6,929,040, which, in turn, claims the benefit of similarly-titled U.S. Provisional Patent Application Ser. No. 60/390,212, filed Jun. 19, 2002; U.S. patent application Ser. No. 13/326,177, filed Dec. 14, 2011, entitled "Device with Penetrable and Resealable Portion and Related Method," which is a continuation of similarly titled U.S. patent application Ser. No. 13/170,613, filed Jun. 28, 2011, now U.S. Pat. No. 8,347,923, which is a continuation of U.S. patent application Ser. No. 12/401,567, filed Mar. 10, 2009, entitled "Device with Needle Penetrable and Laser Resealable Portion and Related Method," now U.S. Pat. No. 7,967,034, which is a continuation of similarly titled U.S. patent application Ser. No. 11/933,300, filed Oct. 31, 2007, now U.S. Pat. No. 7,500,498; U.S. patent application Ser. No. 13/329,483, filed Apr. 30, 2011, entitled "Ready to Feed Container," which is a continuation of International Application Serial No. PCT/US2011/034703, filed Apr. 30, 2011, entitled "Ready to Feed Container and Method," which, in turn, claims the benefit of U.S. Provisional Patent Application Ser. No. 61/330,263 filed Apr. 30, 2010; and U.S. patent application Ser. No. 13/450,306, filed Apr. 18, 2012, entitled "Needle with Closure and Method," which claims the benefit of U.S. Provisional Patent Application Ser. No. 61/476,523, filed Apr. 18, 2011, entitled "Filling Needle and Method." In some such embodiments, at least a portion of the penetrable portion 33 comprises a thermoplastic elastomer that is heat resealable by directing thermal energy or radiation thereto, such as from a laser or other thermal source.

Figure 8C:
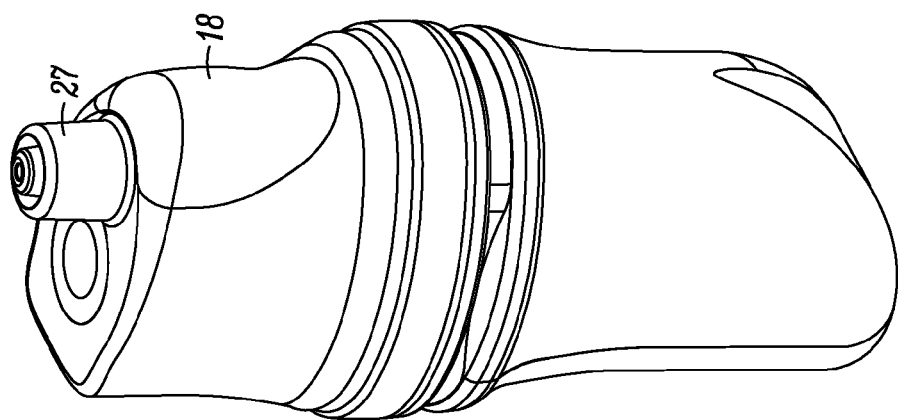
FIG. 8C is a schematic perspective view of the assembled device of FIG. 8A.
Figure 8B:
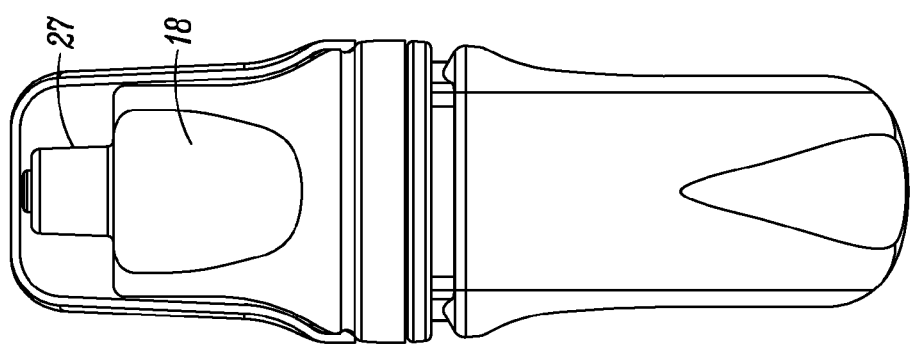
FIG. 8B is a schematic front view of the assembled device of FIG. 8A.
Figure 8A:
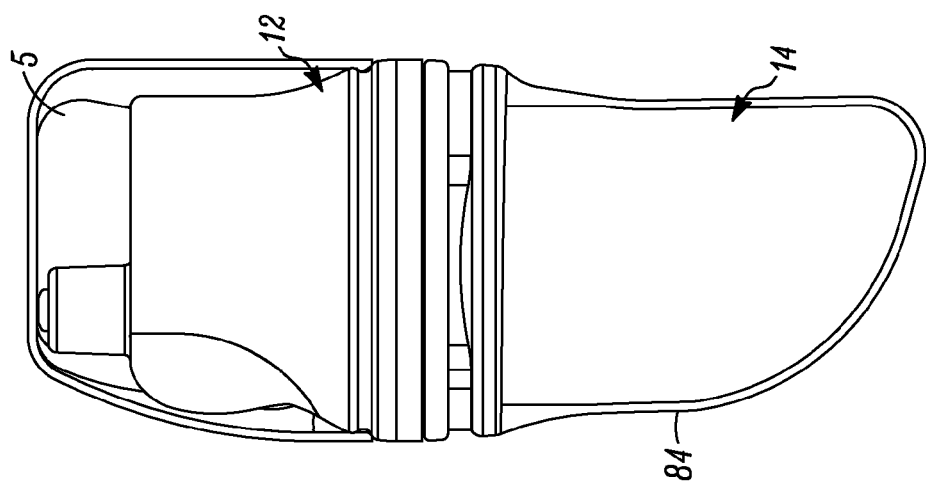
FIG. 8A is a schematic side view of the assembled device, including a first piece, a second piece, a housing and a top cover.

FIGS. 8A-C are schematic views of the assembled device, including a second piece 12, a first piece 14, a housing 84 and a top cover 5. The top cover 5 may be placed on top of the second piece 12 to provide additional protection to the second piece 12 during storage or transport. The top cover 5 may be snap fit, coupled or secured to any portion of the second piece 12, the first piece 14 and the housing 84 as described above, using for example annular grooves and flanges. The top cover 5 may also be used to provide additional sterility to the surfaces of the device 10 when the device 10 is not in use.

As described above, operation of the actuator 18 serves to provide a metered dose of substance 98 from the one-way valve 34 of the device 10. Due to the deflector 25 and the surface finish of the valve seat 24, the device provides an anti-spritz feature that may be useful when the substance is to be dispensed to a body part. For example, if the device 10 includes eye drops or some other saline-based solution for dispensing into the eye of a user, the anti-spritz feature may be desirable to control the velocity of the substance exiting the one-way valve 34. In some embodiments, the one-way valve 34, the valve seat 24 and/or the deflector 25 are configured so that the substance exits the one-way valve 34 at a low velocity. Moreover, each dose may be delivered at a low velocity, which is defined as being low enough so that the user's eye does not receive an impact that could injure the eye. At the same time, if the velocity of the drop is too low than the drop does not have enough force to leave the nozzle and enter a user's eye. Accordingly, an exemplary embodiment of a low velocity is defined as a velocity that is less than about 10 meters per second, and with a preferred range of about 2 meters per second to about 6 meters per second, and with a further preferred range of about 2 meters per second to about 4 meters per second. This may be accomplished in accordance with the teachings of any of the following patents and patent applications, each of which is hereby expressly incorporated by reference in its entirety as part of the present disclosure: U.S. patent application Ser. No. 12/724,370, filed Mar. 15, 2010, entitled "Method for Delivering a Substance to an Eye," which is a continuation of U.S. patent application Ser. No. 10/990,164, filed Nov. 15, 2004, entitled "Delivery Device and Method of Delivery," now U.S. Pat. No. 7,678,089, which, in turn, claims the benefit of similarly titled U.S. Provisional Patent Application Ser. No. 60/519,961, filed Nov. 14, 2003.

In applications requiring the dispensing of a fluid into the eye, each drop can be controlled to deliver a volume within a range of about 15 to about 25 micro liters, and more preferably in the range of about 17 to about 22 micro liters, with each dose being delivered at plus or minus about 5% of the registered or designated volume. This volume of drop allows a maximum amount of fluid to be delivered to an eye without overflowing the cul-de-sac of the eye. This volume of drop also allows the fluid to be delivered without losing visual acuity after the drop is administered to the eye.

By controlling the dosing amount, the device allows for an effective manner in the treatment of dry eye. Specifically, by utilizing the device a dose is administered in the range of about 15 to about 25 micro liters to the ocular cul-de-sac. The dose is then administered four times each day, which equals the approximate amount of an average person's tear production. Accordingly, due to the controlled amount of dosage, and the fact that the maximum amount of fluid is being delivered to the eye without overflowing the cul-de-sac of the eye, the delivery device provides an effective manner in which to treat dry eye.

FIGS. 9 through 12B show another embodiment of a device indicated generally by the reference numeral 210. The dispenser 210 is substantially similar to the dispenser 10 described above with reference to FIGS. 1-8C, and therefore like reference numerals preceded by the numeral "2" are used to indicate like elements.

In the illustrated embodiment, the one-way valve 234 has a valve seat 224 with a generally annular first portion 224a defining a first diameter d1 and a generally annular second portion 224b located adjacent to the first portion 224a and extending toward the exterior of the one-way valve 234 relative to the first portion 224a and defining a second diameter d2 that is less than the first diameter d1. The valve seat 224 further has a partially-annular, e.g., semi-annular, third portion 224c that extends outwardly from the second portion 224b. The valve cover 220 overlies the valve seat 224 to form a normally-closed valve seam 236.

In the illustrated embodiment, where the valve cover 220 overlies the first portion 224a of the valve seat 224, the first portion 224a and the valve cover 220 define an interference fit. As illustrated, the valve cover 220 and the first portion 224a define a first degree of interference 270 towards an upstream end of the first portion 224a, and a second degree of interference 274 at a downstream end of the first portion 224a that is less than the first degree of interference. In the embodiment shown, the degree of interference between the valve cover 220 and first portion 224a uniformly progressively decreases from the first degree of interference 270 to the second degree of interference 274. In other embodiments, the degree of interference decreases in a non-linear fashion. In yet other embodiments, the degree of interference is substantially constant.

Where the valve cover 220 overlies the second portion 224b and third portion 224c of the valve seat 224, the degree of interference is nearly zero or at zero (no interference). Still, the seam 236 along the second portion 224b and third portion 224c is normally closed and prevents the ingress of microbes, air, contaminants or other undesired substances. The decreasing interference along the first portion 224a and the low or absent interference along the second portion 224b and third portion 224c cooperate to prevent any ingress, and also to expel any substance out of the valve 234.

Figure 11:
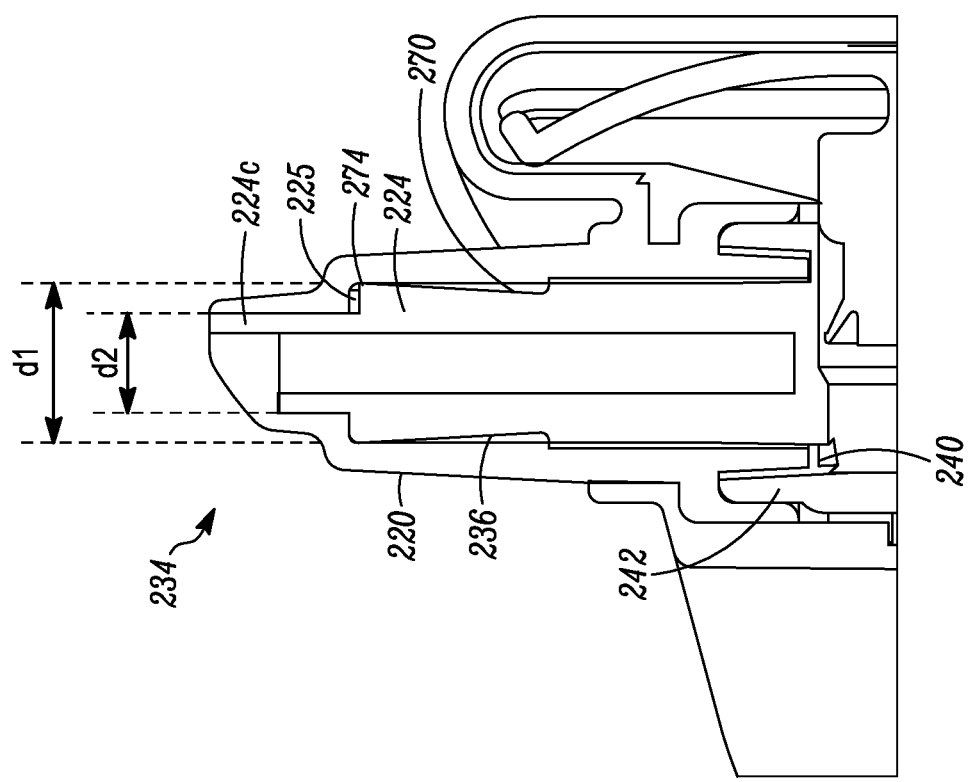
FIG. 11 is an enlarged cross-sectional view of the nozzle portion of the device of FIG. 9.
Figure 12B:
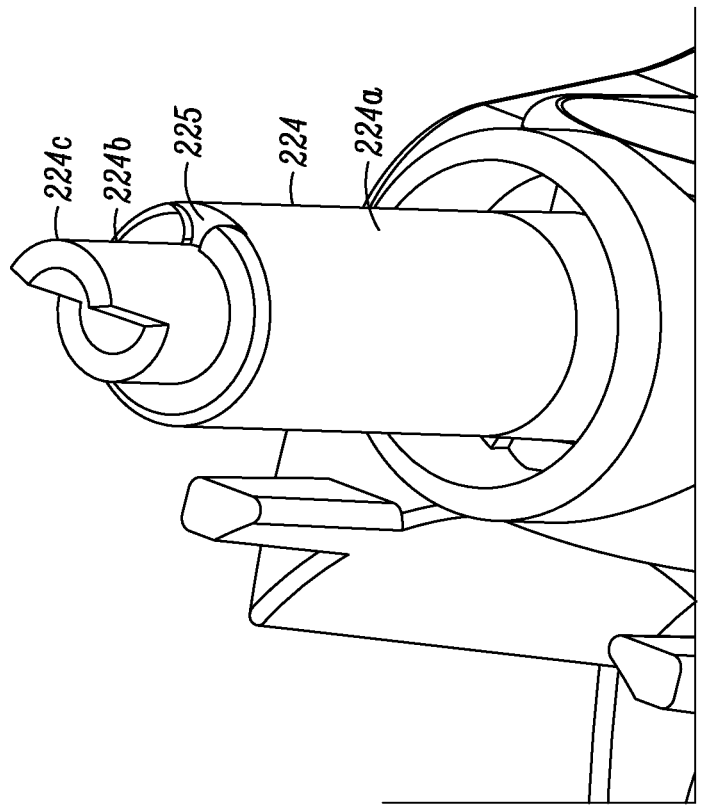
FIG. 12B is an enlarged perspective view of the end portion of the second piece of the device of FIG. 9.
Figure 12A:
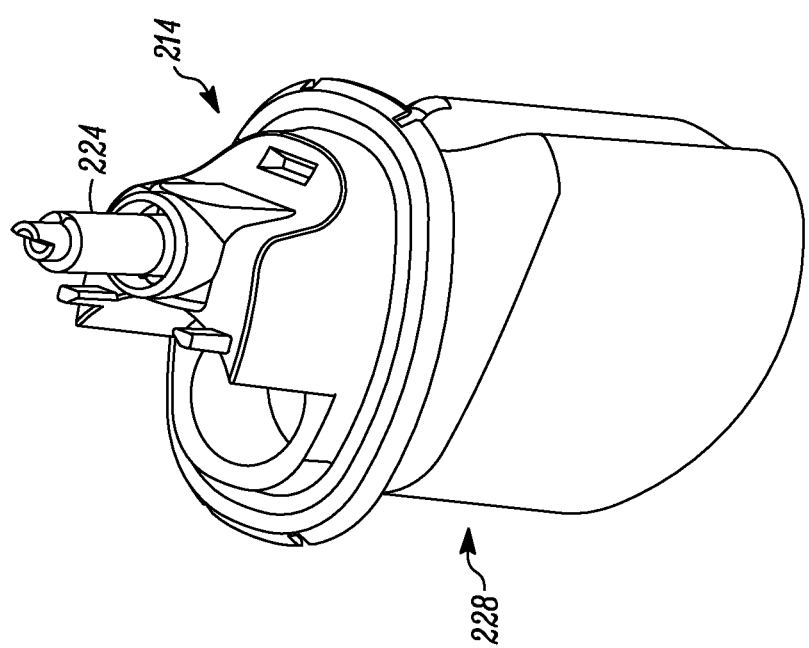
FIG. 12A is a perspective view of the second piece of the device of FIG. 9.

As can be seen in the Figures, the valve cover 220 overlies distal end portions of the first portion 224a and second portion 224b of the valve seat 224. However, as best seen in FIGS. 11 and 12B, the distal end portion of the first portion 224a contains a channel 225 defining a space with the valve cover at that location. Further, the valve cover 220 does not overlie the distal end portion of the third portion 224c. This configuration, in conjunction with the channel 225, causes dispensed fluid to flow through the seam 236 along the first portion 224a, through the channel 225, and through the seam along the second portion 224b and third portion 224c to the exterior of the valve 234. Further, the thin and tooth-like nature of the semi-annular third portion 224c, in combination with the channel 225, guides the substance to exit the valve 234 at that specific location.

As seen in the Figures, the first diameter d1 is discontinuous from the first diameter d2 to form a marked step in diameter where the first portion 224a and the second portion 224b adjoin. When dispensed fluid flows from the larger diameter first portion 224a to the smaller diameter second portion 224b, the velocity of the fluid decreases. The substance thus exits the valve 234 at a lowered velocity, which helps reduce spritzing. The relative diameters of the first portion 224a and second portion 224b (along with the acting diameter of the third portion 224c) may also be configured to assist in reducing the dispensing velocity so as to be suitable for low velocity applications, such as ophthalmic dispensing.

In the embodiment of FIGS. 9-12B, the actuator 218 differs from the actuator 18 of dispenser 10. Whereas in the dispenser 10 the actuator 18 itself defines the spring, in dispenser 210, a spring or resilient member 227 is a separate component from the manually-engageable surface 218a of the actuator 218. In the illustrated embodiment, the spring 227 comprises a curvilinear or bowed resilient member and may be constructed according to means known to those of ordinary skill in the art. Ends 227a, 227b of the spring 227 engage support surfaces 229a, 229b defined by the second piece 212 and first piece 214 respectively. The support surfaces 229a, 229b cooperate with the curvilinear configuration of the spring 227 to bias the actuator 218 toward the rest, ambient or first position.

A compression member or piston 245 is operatively connected to the spring 227 and positioned adjacent to the compression chamber 238 in the rest position. The manually-engageable surface 218a is also operatively connected to the spring 227. In the illustrated embodiment, the manually-engageable surface 218a is positioned adjacent to the spring 227. Upon depressing of the manually-engageable surface 218a by a user, the underside of the manually-engageable surface 218 engages the spring, compressing it, which drives the compression member 245 into the compression chamber 238. As shown, the compression member 245 includes sealing surfaces 245a that sealingly engage lateral surfaces 238a of compression chamber 238. The sealing surfaces 245a form a fluid-tight seal with the lateral surfaces 238a of the compression chamber, sealing the compression chamber 238 upon actuation of the actuator 218. As the compression member 245 moves into the compression chamber 238, it pressurizes the substance in the compression chamber 238 for dispensing through the seam 236 of the valve 234. When the user releases the actuator 218, the compression force of the spring 227 biases the actuator 218 toward the rest position, thereby withdrawing the compression member 245 from the compression chamber 238 and, in turn, drawing additional substance from the storage chamber 230 into the compression chamber 238 through the check valve 242.

In alternative embodiments, rather than sterile filling the device with a needle or other injection member, and resealing the resulting penetration aperture, the device may include a filling valve formed integral and co-molded with the dispensing valve to allow sterile filling of the variable-volume storage chamber through the filling valve, in the same or similar manner to that disclosed any of the following patents and patent applications, each of which is hereby expressly incorporated by reference in its entirety as part of the present disclosure: U.S. patent application Ser. No. 12/534,730, filed Aug. 3, 2009, entitled "Lyophilization Method and Device," now U.S. Pat. No. 8,272,411, which is a continuation of U.S. patent application Ser. No. 11/487,836, filed Jul. 17, 2006, entitled "Container with Valve Assembly and Apparatus and Method for Filling," now U.S. Pat. No. 7,568,509, which is a continuation of U.S. patent application Ser. No. 10/833,371, filed Apr. 28, 2004, entitled "Container with Valve Assembly for Filling and Dispensing Substances, and Apparatus and Method for Filling," now U.S. Pat. No. 7,077,176, which, in turn, claims the benefit of similarly titled U.S. Provisional Patent Application Ser. No. 60/465,992, filed Apr. 28, 2003, and U.S. Provisional Patent Application Ser. No. 60/469,677, filed May 12, 2003, entitled "Dispenser and Apparatus and Method for Filling a Dispenser," and similarly titled U.S. Provisional Patent Application Ser. No. 60/471,592, filed May 19, 2003; U.S. patent application Ser. No. 12/984,482, filed Jan. 4, 2011, entitled "Dispenser and Apparatus and Method for Filling a Dispenser," which is a continuation of similarly titled U.S. patent application Ser. No. 12/025,362, filed Feb. 4, 2008, now U.S. Pat. No. 7,861,750, which is a continuation of similarly titled U.S. patent application Ser. No. 11/349,873, filed Feb. 8, 2006, now U.S. Pat. No. 7,328,729, which is a continuation of similarly-titled U.S. patent application Ser. No. 10/843,902, filed May 12, 2004, now U.S. Pat. No. 6,997,219, which, in turn, claims the benefit of similarly titled U.S. Provisional Patent Application Ser. No. 60/469,677, filed May 12, 2003, and similarly titled U.S. Provisional Patent Application Ser. No. 60/471,592, filed May 19, 2003, and U.S. Provisional Patent Application Ser. No. 60/488,355, filed Jul. 17, 2003, entitled "Piston-Type Dispenser with One-Way Valve for Storing and Dispensing Metered Amounts of Substances, and Pivoting Cover for Covering Dispensing Portion Thereof," and U.S. Provisional Patent Application Ser. No. 60/539,814, filed Jan. 27, 2004, entitled "Piston-Type Dispenser with One-Way Valve for Storing and Dispensing Metered Amounts of Substances;" U.S. patent application Ser. No. 12/701,194, filed Feb. 5, 2010, entitled "Container and Valve Assembly for Storing and Dispensing Substances, and Related Method," which is a continuation of U.S. patent application Ser. No. 11/938,103, filed Nov. 9, 2007, entitled "Device with Chamber and First and Second Valves in Communication Therewith, and Related Method," which is a continuation of U.S. patent application Ser. No. 10/976,349, filed Oct. 28, 2004, entitled "Container and Valve Assembly for Storing and Dispensing Substances, and Related Method," now U.S. Pat. No. 7,637,401, which is a continuation of U.S. patent application Ser. No. 10/640,500, filed Aug. 13, 2003, entitled "Container and Valve Assembly for Storing and Dispensing Substances, and Related Method," now U.S. Pat. No. 6,892,906, and claims priority under 35 U.S.C. §119(e) to U.S. Provisional Patent Application No. 60/403,396, filed Aug. 13, 2002, entitled "Container for Storing and Dispensing Substances and Method of Making Same", and to U.S. Provisional Patent Application No. 60/442,924, filed Jan. 27, 2003, entitled "Container and Valve Assembly for Storing and Dispensing Substances;" and U.S. patent application Ser. No. 12/724,370, filed Mar. 15, 2010, entitled "Method for Delivering a Substance to an Eye," which is a continuation of U.S. patent application Ser. No. 10/990,164, filed Nov. 15, 2004, entitled "Delivery Device and Method of Delivery," now U.S. Pat. No. 7,678,089, which, in turn, claims the benefit of similarly titled U.S. Provisional Patent Application Ser. No. 60/519,961, filed Nov. 14, 2003. In this alternative, the second support of the closure includes co-molded therewith a first integral flexible valve cover and a second integral flexible valve cover. The first support includes a first valve seat and a second valve seat. The first valve cover is superimposed on the first valve seat and forms a dispensing valve as described above, and the second valve cover is superimposed on the second valve seat and forms a filling valve defining a normally closed filling valve seam. Similarly to as described above with respect to the dispensing valve 34, the filling valve may be axially extending and have interference characteristics.

Similarly to as described above, the first support at least partially defines the compression chamber connectable in fluid communication between the variable-volume storage chamber and the inlet to the first dispensing valve seam, and the second support includes an actuator movable between rest, ambient, or first and actuated, depressed or second positions for pressurizing fluid within the compression chamber above the valve opening pressure and, in turn, dispensing the pressurized fluid through the dispensing valve. The dome-shaped or other flexible actuator is formed integral and co-molded with the first and second valve covers.

In the method of forming the device of this alternative embodiment, the step of molding the closure includes co-molding the second support with the first integral flexible valve cover and the second integral flexible valve cover. The step of injection molding the first support includes injection molding the support with the first integral valve seat and the second integral valve seat. The step of assembling the closure to the support includes (i) superimposing the first valve cover on the first valve seat and forming the dispensing valve defining its seam, and (ii) superimposing the second valve cover on the second valve seat and forming the filling valve defining its seam. After the sterilizing step, a filling member, such as a hollow cannula coupled in fluid communication with a pump or pressurized source of product to be sterile filled, is placed in fluid communication with the normally closed valve seam of the filling valve. Then, the substance is sterile filled through the filling member and into the valve seam of the filling valve at a pressure at or above a valve opening pressure thereof and into the variable-volume storage chamber. After the variable-volume storage chamber is sterile filled with the substance, the filling member is withdrawn from the second valve. The seam returns to its normally closed position and the sterile filled substance is maintained hermetically sealed within the variable-volume storage chamber throughout a shelf life and between multiple doses of substance from the variable-volume storage chamber through the first dispensing valve.

Figure 13:
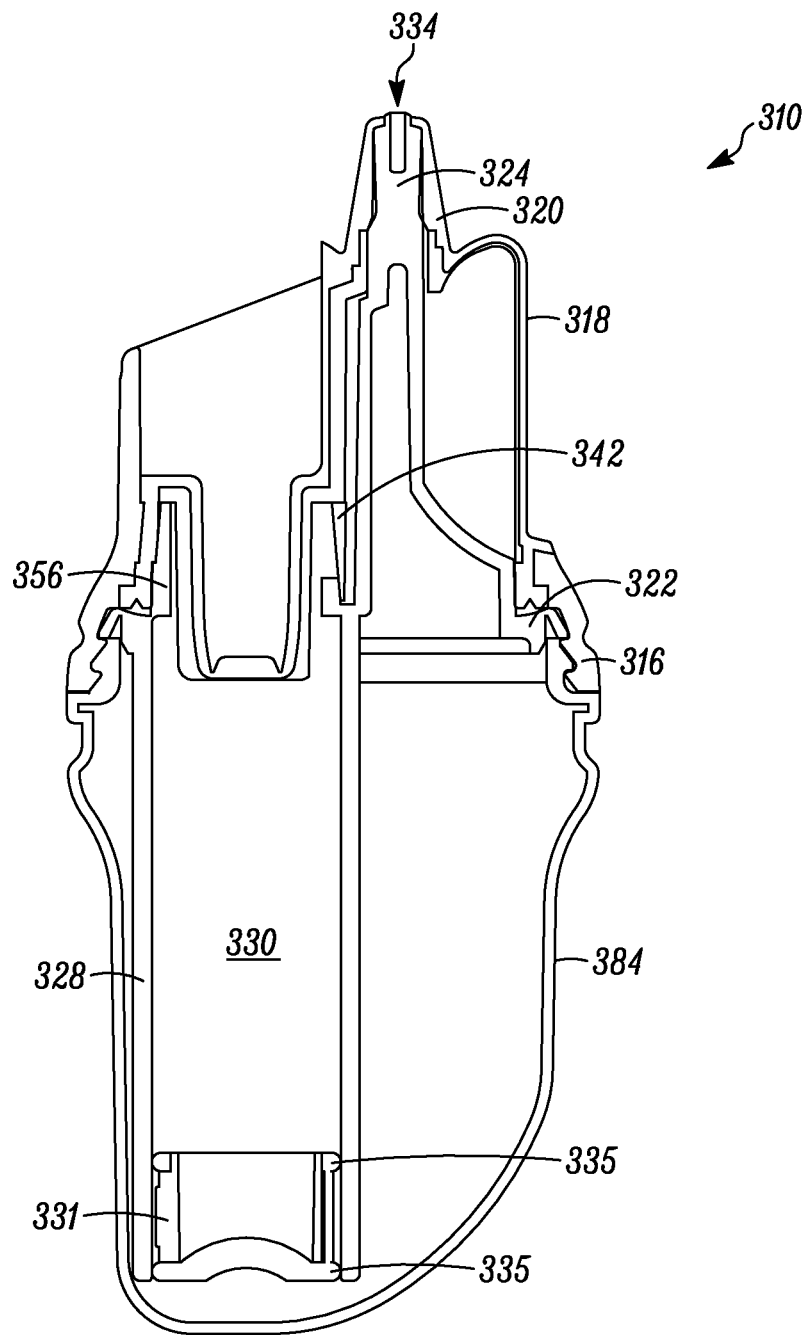
FIG. 13 is a cross-sectional view of another embodiment of a device.

In addition, the variable-volume storage chamber may be formed of any of numerous different materials and configurations, in accordance with any of numerous different manufacturing techniques, which are currently known or later become known. For example, in the embodiment of FIG. 13, the variable volume storage chamber 330 is formed by a seal, stopper, piston or plunger 331 slidably received within a chamber body 328, rather than by a flexible pouch. In the embodiment of FIG. 13, the device is indicated generally by the reference numeral 310. The device 310 is substantially similar to the devices 10, 210 described above in connection with FIGS. 1-12B, and thus like reference numerals preceded by the numeral "3" are used to indicate like elements. For simplicity, the following description is directed to the differences in the variable-volume storage chamber 330 from the storage chambers 30, 230.

As shown in FIG. 13, the chamber body 328 is integrally formed, e.g. molded, with, and extends from, the boss 356 of the first support 322. The sliding seal 331, received within the chamber body 328, is spaced away from the boss 356. In other embodiments, though, the chamber body is not formed with and/or does not extend from the boss 356, but is connected or connectable in fluid communication with the boss so as to be filled and/or dispense fluid through the boss or other inlet/outlet. The sliding seal includes at least one, and in the embodiment shown, two axially spaced outer sealing members or portions 335 that sealingly engage the interior wall of the chamber body 328 to form a fluid-tight seal therebetween, but permit the sliding seal 331 to slide within the chamber body 328. In the illustrated embodiment, the chamber body 328, and therefore the interior wall thereof, is cylindrical, and the sliding seal 331, and thus the sealing member(s) 335 thereof, is correspondingly shaped. However, as should be understood, the chamber body and the sliding seal may define other corresponding configurations. The sealing member(s) or portion(s) 335 may be formed integral with the sliding seal 331, such as by forming thereon annular protuberances, as shown, or may be formed by sealing members, such as o-rings or other sealing members, that are received within corresponding grooves or recesses formed in the sliding seal.

The sliding seal 331 and the manner in which it cooperates with the chamber body 328 to define the variable-volume storage chamber 330 may be the same as or substantially similar to that disclosed in any of the following patents and patent applications, each of which is hereby expressly incorporated by reference in its entirety as part of the present disclosure: U.S. patent application Ser. No. 13/219,597, filed Aug. 26, 2011, entitled "Laterally-Actuated Dispenser with One-Way Valve For Storing and Dispensing Substances," which is a continuation of U.S. patent application Ser. No. 12/710,516, filed Feb. 23, 2010, entitled "Laterally-Actuated Dispenser with One-Way Valve for Storing and Dispensing Metered Amounts of Substances," now U.S. Pat. No. 8,007,193, which is a continuation of similarly titled U.S. patent application Ser. No. 11/237,599, filed Sep. 27, 2005, now U.S. Pat. No. 7,665,923, which, in turn, claims the benefit of similarly titled U.S. Provisional Patent Application No. 60/613,583, filed Sep. 27, 2004, and similarly titled U.S. Provisional Application No. 60/699,607 filed Jul. 15, 2005; U.S. patent application Ser. No. 13/743,661, filed Jan. 17, 2013, entitled "Multiple Dose Syringe and Method," which, in turn, claims the benefit of similarly titled U.S. Provisional Patent Application No. 61/587,500, filed Jan. 17, 2012; and U.S. patent application Ser. No. 13/744,379 entitled "Multiple Dose Vial and Method," filed on Jan. 17, 2013, which, in turn, claims the benefit of similarly titled U.S. Provisional Patent Application No. 61/587,525, filed Jan. 17, 2012.

Substance can be dispensed from the variable-volume storage chamber 330 in similar manner as described above in connection with the embodiments of FIGS. 1-12B. As substance is dispensed from the storage chamber 330, suction forces exerted on the sliding seal 331 caused by the exit of the substance from the storage chamber 330 cause the seal 331 to move or slide within the chamber body 328, e.g., axially, toward the boss 356, to reduce the volume of the variable-volume storage chamber 330 by substantially the same volume of substance dispensed.

Figure 14:
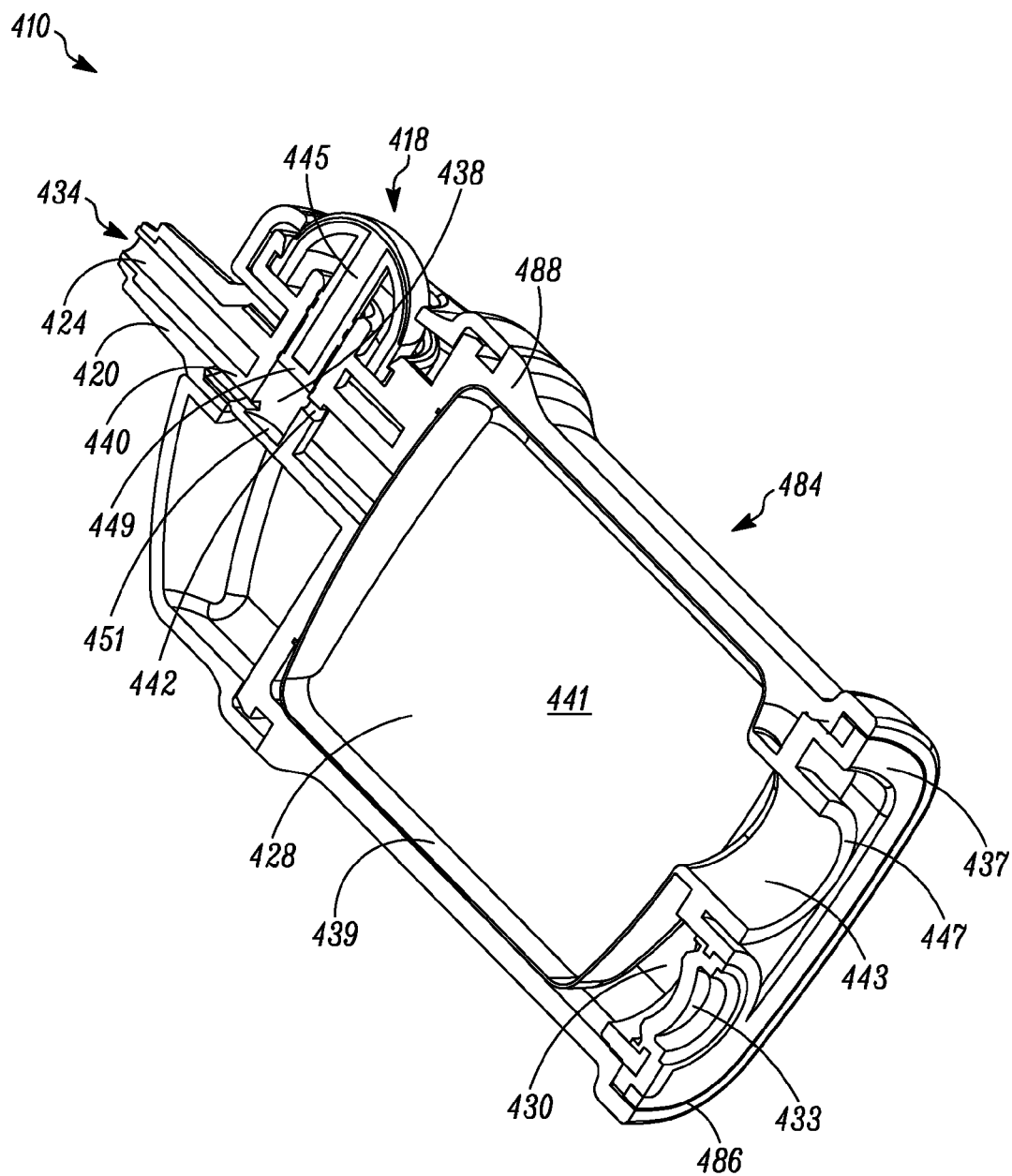
FIG. 14 is a perspective cross-sectional view of another embodiment of a device.

Alternatively, in other embodiments the device may include a collapsible and flexible bladder or pouch received within a device housing, where the variable volume storage chamber is defined between the bladder and the surrounding housing. One example of such an embodiment is shown in FIG. 14. In this illustrated embodiment, the device is indicated generally by the reference numeral 410. The device 410 is substantially similar to the devices 10, 210, and 310 described above in connection with FIGS. 1-13, and thus like reference numerals preceded by the numeral "4" are used to indicate like elements. For simplicity, the following description is directed to the differences between the embodiment of FIG. 14 and the previously described embodiments.

As shown in FIG. 14, the device 410 includes a collapsible flexible bladder 428 integrally formed with, and projecting from, a base closure 437. The base closure 437 sealingly encloses an open base end 486 of the device housing 484, the thereby sealing off the storage chamber 430 from the ambient atmosphere. The flexible bladder 428 projects within the housing 484 toward the upper support 488 thereof, secured to the second support 416. The variable-volume storage chamber 430 is defined between the flexible bladder 428 and the side wall of the housing 484. The flexible bladder 428 has a bladder wall 439 defining a bladder cavity 441 therein. The flexible bladder 428 has an opening 443 at a base end thereof, defining an open port 447 in the base closure 437 in fluid communication with the bladder cavity 441. Alternatively, in other embodiments, the bladder 428 may extend from the second support 416 toward the base end 486 of the housing 484, or from the housing 484, with the open port formed in the second support or the housing, respectively.

In the illustrated embodiment, the base closure 437 and a preform (not shown) for the flexible bladder 428 are injection molded, and the bladder 428 is, in turn, blow molded from the injection molded preform, in accordance with the teachings of any of the patents and patent applications incorporated by reference above. In other embodiments, the bladder 428 is sealed and elastic, and thus compressible and expandable.

The flexible bladder 428 defines an external shape dimensioned to fit within the housing 484 when in the fully expanded state as shown in FIG. 14. In the fully expanded state, the wall 439 of the bladder 428 defines a shape or morphology substantially the same as that of the side wall of the housing 484 so that it conforms to and contacts the housing sidewall substantially throughout the interface of these two components. In this state, the empty variable-volume storage chamber 430 is substantially airless.

The storage chamber 430 is sterile or aseptically filled with multiple doses of the substance to be dispensed via the penetrable and resealable portion 433, which alternatively may be a filling valve, in similar manner as in the embodiments described above. In the illustrated embodiment, the penetrable and resealable portion 433 is located in the base closure 437, adjacent the port 447. However, the portion 433 may equally be located in the second piece 412, as in the above-described embodiments, or alternatively, along the sidewall of the housing 484. As the storage chamber 430 is filled with the substance, the substance displaces the bladder and the bladder 428 collapses. Thereafter, as each dose of substance is dispensed from the variable-volume storage chamber 430, the bladder 428 inflates accordingly as further described below. The bladder 428 is expandable until the bladder wall 439 substantially conforms to the morphology of the side wall of the housing 484, to thereby eliminate any ullage or dead space and dispense substantially all of the substance in the storage chamber 430.

The sealed interior of the device housing 484, comprised of the variable-volume storage chamber 430 and the flexible bladder 428, defines a constant volume. As the volume of the storage chamber 430 increases, the volume of the flexible bladder cavity 441 substantially correspondingly decreases, and likewise, as the volume of the storage chamber 430 decreases, the volume of the flexible bladder cavity 441 substantially correspondingly increases.

As shown in FIG. 14, the flexible bladder 428 is assembled into the device housing 484 in its fully expanded state. Any air in the housing 484 is thus displaced out the base of the housing 484 during assembly. Thereafter, when the sealed variable-volume storage chamber 430 is filled with a desired volume of substance, i.e., when substance is filled between the side wall of the housing 484 and the flexible bladder 428, the flexible bladder 428 collapses accordingly, where a substantially equal volume of air flows out of the bladder cavity 441, through the open port 447, and into the ambient atmosphere. Afterwards, when a dose of the substance within the variable-volume storage chamber 430 is dispensed therefrom, through the valve 434, the pressure differential between the variable-volume storage chamber 430 and the atmosphere causes a substantially equal volume of air to flow into the bladder cavity 441, through the port 447, and re-expand the bladder. In some embodiments, a one-way valve is inserted into the open port 447 of the base closure 437 after the variable-volume storage chamber 430 is filled with the substance and the bladder 428 is collapsed. The one-way valve allows air to flow into the bladder cavity 441 with each dose of substance dispensed, but substantially prevents air from flowing out of the cavity. As may be recognized by those of ordinary skill in the pertinent art based on the teachings herein, the one-way valve may take the form of any of numerous different one-way valves, that are currently known, or that later become known, for performing the function of the one-way valve as described herein, including without limitation a check valve, a duckbill valve, a flapper valve or an umbrella valve.

In the embodiment of FIG. 14, the actuator 418 also differs from the actuators 18, 218 and 318 of the above-described embodiments. Rather than having a valve between the storage chamber 430 and the compression chamber 438, a fluid passageway 442 extends between the outlet of the storage chamber 430 and the inlet of the compression chamber 438 for permitting the flow of fluid or other substance between the storage chamber 430 and into the compression chamber 438. As shown, the actuator 418 defines an integral spring, approximately dome-shaped in the illustrated embodiment, and includes a compression member or piston 445 operatively connected thereto and receivable within the compression chamber 438. The piston 445 is movable between a rest, ambient or first position, as shown in FIG. 14, where the piston tip 449 is positioned adjacent from the upstream end of compression chamber 438 and thus spaced away from the compression chamber outlet/valve inlet 440, and a second fully-actuated position with the piston tip 449 located adjacent to, or in contact with a stop surface 451 formed at the downstream end of the compression chamber 438, adjacent the chamber outlet 440. The compression chamber 438 defines a diameter or width selected to cooperate with the piston tip 449 to define the volume of the chamber 438 and thus the volume of the dosage dispensed. The extent of the chamber 438 in combination with the travel of the piston tip 449 defines a compression zone within which the fluid or other substance is compressed by the piston 445 and, in turn, forced through the one-way valve 434. When the actuator 418 is depressed, thereby moving the piston 445 from the resting position toward the fully-actuated position, the peripheral surface of the piston tip 449 slidably and sealingly, e.g., via an interference fit, engages the wall of compression chamber 438 and forms a substantially fluid-tight seal therebetween.

In the rest or ambient position, when the actuator is unactuated, the piston tip 449 is spaced away from the fluid passageway 442, thereby allowing fluid communication between the storage chamber 430 and the compression chamber 438. Thus fluid is permitted to flow both forwardly in front of the piston 445, and rearwardly back over the sides of the piston tip 449. When a user depresses the actuator, thereby moving the piston 445 from the rest position, into the compression chamber 438 and toward the fully-actuated position, and upon sealing engagement of the piston tip 449 with the wall of the compression chamber 438, the fluid passageway 442 is sealed off by the piston 445, thereby trapping a substantially precise volume of fluid within the compression chamber 438. As the piston 445 continues its movement toward the stop surface 451, thereby increasing the pressure within the sealed compression chamber 438 to a pressure exceeding the valve opening pressure, the substance therein is forced out of the compression chamber 438, through the valve inlet 440 and through the valve 434. When the user releases the actuator 418, the compression force of the integral spring biases the actuator 418 toward the rest position, thereby withdrawing the piston 445 from the compression chamber 438 and, in turn, re-opening the fluid passageway 442. As the fluid passageway is reopened, additional substance from the storage chamber 430 is drawn into the compression chamber 438 due to the pressure differential between the compression chamber 438 and the storage chamber 430.

In the illustrated embodiment, the actuator 418 is laterally positioned with respect to the one-way valve 434. The piston 445 defines a drive axis extending between the rest position and the fully-actuated position, and the piston drive axis is oriented substantially transverse to the axis of the one-way valve 434 and device housing 484. In the illustrated embodiment, the piston drive axis is oriented at about 90° relative to the axis of the one-way valve and housing. However, the drive axis may be oriented at any of numerous angular orientations in order to facilitate the manufacture of the device, to facilitate manual manipulation of the device, or otherwise to improve the ergonomics thereof.

One advantage of the devices and methods of the present invention is that the device may be manufactured in essentially two parts forming a sealed, empty, sterile variable-volume storage chamber that is ready for aseptic filling by needle penetration and resealing by liquid sealant or by any of numerous other sterile filling methods or devices that are currently known, or that later become known. Yet another advantage is that the housing or outer body may be formed of a relatively inexpensive material, such as recycled plastic, cardboard, or other biodegradable materials, that after use may be automatically disassembled into (1) the collapsed plastic bag and closure that can be recycled, and (2) the outer bottle or body which can be biodegradable. Alternatively, the housing can be reusable such that the collapsed pouch and closure can be removed from the housing, and a fresh pouch and enclosure can be inserted into the housing as many times as desired.

A significant advantage of the various embodiments described herein is that the following features are provided utilizing only two parts: zero ingress in a multi-dose delivery system; a non-contamination valve; a sterile filling port; a metering dose pump; a collapsible pouch defining a sealed, variable-volume storage chamber; and a compression chamber in fluid communication between the variable-volume storage chamber and the non-contamination valve and forming part of the metering dose pump. Yet another advantage is that one can use this two piece collapsible assembly or add a more rigid outer container, e.g., that is completely biodegradable, re-usable and/or recyclable, to protect the pouch or for aesthetic purposes. A still further advantage is that the unique valve prevents any ingress of any germs, bacteria or other unwanted substances, and thus prevents contamination of the product stored within the interior of the device which, in turn, may significantly increase the stability of the product. A still further advantage is that there is no need to refrigerate the container or other device, even after multiple dose delivery, since the variable-volume storage chamber remains hermetically sealed and each dose is sterile from the first to the last. Another advantage is that the package provides a unique means to reduce the carbon foot print of the packaging in comparison to prior art packages. For example, there is no need to re-heat the product after filling (such as with retort processing), and there is no need to refrigerate the product or container after dispensing or between dispensing multiple doses over extended periods of time. Yet another advantage is that the invention provides a high, and even unmatched, safety level assurance in a very price-competitive package.

It should be understood that the terms "about," "substantially," "approximately," "generally" and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

As may be recognized by those of ordinary skill in the pertinent art based on the teachings herein, numerous changes may be made to the above-described and other embodiments of the present invention without departing from the scope of the invention. For example, the device may be sterile filled in any of numerous different ways, including by needle penetration and laser resealing, or valve-in filling. The actuator, one-way valve, housing and other components of the device may be formed of any of numerous different materials or combinations of materials, may take any of numerous different shapes and/or configurations, and may be manufactured in accordance with any of numerous different methods or techniques, that are currently known or that later become known. In addition, the devices may include few or more components or features than the embodiments described herein. Further, the variable-volume storage chamber may be formed of any of numerous different materials or configurations, in accordance with any of numerous different manufacturing techniques, that are currently known or that later become known. In addition, the term "semi-annular" is used herein to mean a portion of, or less than 360° of a surface, but does not require that the surface be circular or defined by a portion of a circle. Rather, the semi-annular surface may be curvilinear in part and/or substantially flat in part. Accordingly, this detailed description of currently preferred embodiments is to be taken in an illustrative as opposed to limiting sense.

What is claimed is:

1. A device comprising:
   an integral first piece including a storage chamber adapted for storing a substance therein, an opening in fluid communication with the storage chamber defining one or more of an inlet to or an outlet from the storage chamber, and an elongated generally annular valve seat;
   an integral second piece defining a closure configured to seal an interior of the storage chamber with respect to ambient atmosphere with the second piece engaged with the first piece, and including
   (1) a penetrable and resealable portion axially aligned with and in fluid communication with said opening, and configured to receive therethrough an injection or filling member for filling the storage chamber with substance; and
   (2) an elongated generally annular flexible valve member configured to sealingly engage the valve seat with the second piece engaged with the first piece to define a one way valve defining an elongated, generally annular, normally closed valve seam between the valve seat and the valve member, an inlet at one end of the seam, an outlet spaced relative to the inlet at another end of the seam to define an outlet of the device, and a valve opening pressure;

wherein the valve member is moveable in response to substance at the inlet exceeding the valve opening pressure between (i) a first position with the valve member and valve seat forming the normally closed seam and (ii) a second position with at least a portion of the valve member spaced away from the valve seat to allow the substance to pass through the valve seam from the inlet and to dispense the substance through the outlet at the another end of the valve seam and out of the device.

2. A device as defined in claim 1, further comprising a pump configured to pump substance through the one way valve.

3. A device as defined in claim 2, wherein the pump comprises a compression chamber connectible in fluid communication between the storage chamber and the inlet to the valve seam and at least partially formed by a portion of the first piece and an actuator mounted on the second piece movable between first and second positions for pressurizing substance within the compression chamber above the valve opening pressure and, in turn, dispensing pressurized substance through the one way valve.

4. A device as defined in claim 3, wherein during movement of the actuator in a direction from the second position toward the first position, the storage chamber is in substance communication with the compression chamber for permitting substance to flow from the storage chamber into the compression chamber, and during movement of the actuator in a direction from the first position toward the second position, substance is pressurized above the valve opening pressure and, in turn, dispensed through the one way valve and out of the device.

5. A device as defined in claim 4, further comprising an actuating device for actuating the actuator.

6. A device as defined in claim 5, wherein the actuating device includes a manually engageable surface configured for manual engagement to move the actuator between the first and second positions.

7. A device as defined in claim 3, wherein the actuator comprises a flexible member.

8. A device as defined in claim 3, wherein the actuator is biased in a direction from the second position toward the first position.

9. A device as defined in claim 8, further including a biasing member or spring adapted to bias the actuator.

10. A device as defined in claim 9, wherein the biasing member or spring is one of (i) integral with the actuator and (ii) separate from the actuator.

11. A device as defined in claim 3, wherein the one way valve defines a dispensing axis substantially along which substance is dispensed from the valve, and movement of the actuator between the first and second positions defines a direction that is one or more of (i) substantially perpendicular to or (ii) at an acute angle to the dispensing axis.

12. A device as defined in claim 3, wherein the compression chamber defines a volume approximately equal to a dose of the substance, and moving the actuator from the first position to the second position substantially dispenses a dose of substance though the one-way valve.

13. A device as defined in claim 12, wherein the valve is configured to dispense the dose in the form of a drop.

14. A device as defined in claim 12, wherein the volume of the compression chamber is configured so that the dose is between approximately 15 and approximately 25 micro liters.

15. A device as defined in claim 1, wherein the second piece includes a shield extending around at least a portion of the valve seat and spaced sufficiently therefrom to permit the valve member to move into the second position.

16. A device as defined in claim 1, wherein the first and second pieces are slidingly engaged with each other.

17. A device as defined in claim 1, wherein the device defines an axis, and the one way valve defines a dispensing axis substantially along which substance is dispensed from the valve, wherein the dispensing axis is one of (i) substantially aligned with and (ii) substantially parallel to the device axis.

18. A device as defined in claim 1, wherein the valve seat includes a tip extending past the valve member configured to substantially prevent residue collection at the outlet of the valve seam.

19. A device as defined in claim 1, wherein the flexible valve member is formed of an elastomeric material that exhibits substantially zero creep.

20. A device as defined in claim 19, wherein the elastomeric material is a silicone.

21. A device as defined in claim 19, wherein the elastomeric material includes an antimicrobial additive.

22. A device as defined in claim 21, wherein the elastomeric material is a silicone elastomer including a silver-based antimicrobial additive.

23. A device as defined in claim 1, wherein the one way valve is configured to reduce spritzing of substance dispensed out of the device.

24. A device as defined in claim 23, wherein the valve seat includes a rough surface finish configured to reduce tackiness.

25. A device as defined in claim 23, wherein the valve member comprises a deflector configured to control velocity of substance exiting the one way valve, the deflector one or more of (i) disposed over at least a portion of an end surface of the valve seat or (ii) extends beyond the valve seat and bends inwardly over at least a portion of an end surface of the valve seat.

26. A device as defined in claim 23, wherein the valve seat defines a first portion having a first diameter and a second portion adjacent to a downstream end of the first portion having a second diameter that is less than and discontinuous with the first diameter.

27. A device as defined in claim 1, wherein the valve is configured to dispense substance through the outlet substantially at a selected annular location thereof.

28. A device as defined in claim 27, wherein the valve seat further comprises a partially or semi-annular portion at the outlet.

29. A device as defined in claim 1, wherein at least one internal surface of the device configured to contact the substance comprises material that one or more of (a) does not absorb any component of the substance or (b) is not adsorbed into the substance.

30. A device as defined in claim 29, wherein said material does not absorb any component of prostaglandins and is not adsorbed into prostaglandins.

31. A device as defined in claim 29, wherein said material is polypropylene.

32. A device as defined in claim 1, further comprising at least one drug protection portion overlying an at least one internal surface of the device configured to contact the substance and comprising material that one or more of (a) do not absorb any component of the substance or (b) are not adsorbed into the substance.

33. A device as defined in claim 32, wherein said at least one drug protection portion does not absorb any component of prostaglandins and is not adsorbed into pro staglandins.

34. A device as defined in claim 32, wherein said material is polypropylene.

35. A device as defined in claim 1, wherein the penetrable and resealable portion is resealable by one or more of a liquid sealant or the application of radiation or energy thereto.

36. A device as defined in claim 1, wherein the storage chamber is a variable-volume storage chamber.

37. A device as defined in claim 36, wherein the variable-volume storage chamber is defined by a collapsible bladder.

38. A device as defined in claim 37, further comprising a housing engaged with the second piece and including the storage chamber therein.

39. A device as defined in claim 38, wherein the collapsible bladder is received within the housing and the variable-volume storage chamber is defined between the flexible bladder and the housing.

40. A device as defined in claim 37, wherein the bladder is blow molded from a preform.

41. A device as defined in claim 36, wherein the first piece further comprises a body including a sliding seal slidingly received therein and slidably moveable relative to the closure, and the variable-volume storage chamber is defined within the body between the sliding seal and the closure.

42. A device as defined in claim 1, wherein the valve member and valve seat define an interference fit therebetween.

43. A device as defined in claim 42, wherein the degree of interference between the valve member and valve seat decreases in a direction from the inlet of the valve seam toward the outlet thereof.

44. A device as defined in claim 1, wherein in the first position the one way valve substantially prevents the ingress of bacteria or germs in the direction from the valve seam outlet toward the inlet.

45. A device as defined in claim 3, wherein the flexible valve member and the actuator are co-molded.

46. A device as defined in claim 1, wherein the valve seat is co-molded with the first piece.

47. A device as defined in claim 1, wherein one or more of (i) the valve member defines a generally inwardly tapered cross-sectional shape in a direction from the inlet toward the outlet of the valve seam or (ii) the valve seat defines a generally outwardly tapered cross-sectional shape in the direction from the inlet toward the outlet of the valve seam.

48. A device as defined in claim 1, wherein the outlet of the valve seam is located at an exterior of the device.

49. A device as defined in claim 1, wherein the outlet of the elongated, generally annular, normally closed valve seam is spaced axially relative to the inlet of the elongated, generally annular, normally closed valve seam.

50. A device as defined in claim 35, wherein the second piece further defines a recess adapted to receive an amount of liquid sealant to hermetically seal with liquid sealant a penetration aperture in the penetrable and resealable portion resulting from penetration thereof by an injection or filling member.

51. A device comprising:
  integral first means for including second means for storing a substance therein, and including an opening in fluid communication with the second means defining one or more of an inlet to or an outlet from the second means;
  integral third means for sealing an interior of the second means with respect to ambient atmosphere with the third means engaged with the first means, and for including fourth means for sealingly engaging fifth means of the first means with the third means engaged with the first means to define sixth means having normally closed seventh means, the integral third means including a penetrable and resealable portion axially aligned with and in fluid communication with said opening, and configured to receive therethrough an injection or filling member for filling the second means;
  wherein the fourth means is also for moving in response to substance at an inlet to the seventh means exceeding a valve opening pressure of the sixth means from a first position forming the normally closed seventh means to a second position for allowing substance to pass through the sixth means for dispensing substance through an outlet end of the seventh means and out of the device.

52. A device as defined in claim 51, further comprising eighth means for pumping substance through the sixth means.

53. A device as in claim 52, wherein the first means comprises a first piece, the second means comprises a storage chamber, the third means comprises a second piece, the fourth means comprises a elongated generally annular flexible valve member, the fifth means comprises an elongated generally annular valve seat, the sixth means comprises a one way valve, the seventh means comprises a elongated, generally annular, normally closed valve seam, and the eighth means comprises a pump.

54. A device as defined in claim 51, wherein the penetrable and resealable portion is resealable by one or more of a liquid sealant or the application of radiation or energy thereto.

55. A device as defined in claim 54, wherein the integral third means further defines a recess adapted to receive an amount of liquid sealant to hermetically seal with liquid sealant a penetration aperture in the penetrable and resealable portion resulting from penetration thereof by an injection or filling member.

56. A method comprising:
  (a) engaging an integral first piece with an integral second piece, wherein
  the integral first piece includes a storage chamber adapted for storing a substance therein, an opening in fluid communication with the storage chamber defining one or more of an inlet to or an outlet from the storage chamber, and an elongated generally annular valve seat; and
  the integral second piece defines a closure configured to seal an interior of the storage chamber with respect to ambient atmosphere with the second piece engaged with the first piece, and further including (1) a penetrable and resealable portion axially aligned with and in fluid communication with said opening, and configured to receive therethrough an injection or filling member for filling the storage chamber with substance; and (2) an elongated generally annular flexible valve member configured to sealingly engage the valve seat with the second piece engaged with the first piece to define a one way valve defining an elongated, generally annular, normally closed valve seam between the valve seat and the valve member, an inlet at one end of the seam, an outlet spaced relative to the inlet at another end of the seam to define an outlet of the device, and a valve opening pressure;
(b) sealing an interior of the storage chamber with respect to ambient atmosphere with the closure;
(c) superimposing the valve member onto the valve seat; and
(d) forming an elongated, generally annular, normally closed valve seam between the valve seat and the valve member, wherein the valve member is moveable in response to substance at the inlet exceeding the valve opening pressure between (i) a first position with the valve member and valve seat forming the normally closed seam and (ii) a second position with at least a portion of the valve member spaced away from the valve seat to allow the substance to pass through the valve seam from the inlet and to dispense the substance through the outlet at the another end of the valve seam and out of the device.

57. A method as defined in claim 56, wherein steps (b) through (d) occur during step (a).

58. A method as defined in claim 56, further comprising providing the first piece, which includes injection molding a support and integral storage chamber pre-form and blow molding the pre-form, but not the support, into an expanded shape forming a pouch, at least a portion of which is flexible to define the storage chamber to be a variable-volume storage chamber.

59. A method as defined in claim 57, further comprising collapsing the variable-volume storage chamber prior to step (a).

60. A method as defined in claim 59, further comprising sterile or aseptically filling the collapsed variable volume storage chamber.

61. A method as defined in claim 60, further comprising sterilizing the sealed variable-volume storage chamber prior to said filling.

62. A method as defined in claim 56, further comprising providing the second piece, which includes molding the closure and co-molding or over-molding the valve cover therewith.

63. A method as defined in claim 62, further comprising co-molding or over-molding an actuator with the closure.

64. A method as defined in claim 63, further comprising the step of:
(e) forming a compression chamber between the actuator and the first piece.

65. A method as defined in claim 64, wherein step (e) occurs during step (a).

66. A method as defined in claim 56, further comprising the steps of storing substance in the storage chamber and dispensing substance through and out of the seam substantially without spritzing of the substance.

67. A method as defined in claim 56, further comprising storing substance in the storage chamber and dispensing substance through and out of the seam substantially at a selected annular location thereof.

68. A method as defined in claim 56, further comprising storing pro staglandins in the storage chamber substantially without one or more of (a) absorbing any component of the prostaglandins by the storage chamber or (b) adsorbing any material of the storage chamber into the pro staglandins.

69. A method as defined in claim 56, wherein step (a) comprises slidingly engaging the first and second pieces together.

70. A method as defined in claim 56, wherein the penetrable and resealable portion is resealable by one or more of a liquid sealant or the application of radiation or energy thereto.

71. A method as defined in claim 70, wherein the second piece further defines a recess adapted to receive an amount of liquid sealant to hermetically seal with liquid sealant a penetration aperture in the penetrable and resealable portion resulting from penetration thereof by an injection or filling member.

* * * * *

UNITED STATES PATENT AND TRADEMARK OFFICE
CERTIFICATE OF CORRECTION

| | | |
|---|---|---|
| PATENT NO. | : 9,737,435 B2 | Page 1 of 1 |
| APPLICATION NO. | : 13/745721 | |
| DATED | : August 22, 2017 | |
| INVENTOR(S) | : Daniel Py | |

It is certified that error appears in the above-identified patent and that said Letters Patent is hereby corrected as shown below:

In the Claims

Claim 12, Column 29, Line 65, "though" should be changed to --through--

Claim 33, Column 31, Line 6, "pro staglandins" should be changed to --prostaglandins--

Claim 68, Column 34, Line 24, "pro staglandins" should be changed to --prostaglandins--

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*